United States Patent
Lam et al.

(10) Patent No.: US 7,416,554 B2
(45) Date of Patent: Aug. 26, 2008

(54) APPARATUS AND METHODS FOR FORMING AND SECURING GASTROINTESTINAL TISSUE FOLDS

(75) Inventors: Cang Lam, Irvine, CA (US); Rich Ewers, Fullerton, CA (US); Alexander Khairkhahan, Palo Alto, CA (US); Vahid C. Saadat, Saratoga, CA (US)

(73) Assignee: USGI Medical Inc, San Clemente, CA (US)

( * ) Notice: Subject to any disclaimer, the term of this patent is extended or adjusted under 35 U.S.C. 154(b) by 526 days.

(21) Appl. No.: 10/672,375

(22) Filed: Sep. 25, 2003

(65) Prior Publication Data

US 2004/0147958 A1 Jul. 29, 2004

Related U.S. Application Data

(63) Continuation-in-part of application No. 10/639,162, filed on Aug. 11, 2003, and a continuation-in-part of application No. 10/612,170, filed on Jul. 1, 2003.

(60) Provisional application No. 60/500,627, filed on Sep. 5, 2003, provisional application No. 60/433,065, filed on Dec. 11, 2002.

(51) Int. Cl.
*A61B 17/08* (2006.01)
*A61B 17/04* (2006.01)

(52) U.S. Cl. ...................... 606/153; 606/232

(58) Field of Classification Search ............ 606/151, 606/153, 232, 213, 215, 216, 220, 221, 139, 606/144, 145, 148, 72; 227/66, 67; 600/104
See application file for complete search history.

(56) References Cited

U.S. PATENT DOCUMENTS

| 2,201,610 A | 5/1940 | Dawson, Jr. |
| 2,413,142 A | 12/1946 | Jones et al. |
| 3,150,379 A | 9/1964 | Brown |
| 3,166,072 A | 1/1965 | Sullivan, Jr. |
| 3,494,006 A | 2/1970 | Brumlik |
| 3,551,987 A | 1/1971 | Wilkinson |
| 3,646,615 A | 3/1972 | Ness |

(Continued)

FOREIGN PATENT DOCUMENTS

EP   0 480 428 A2   4/1992

(Continued)

OTHER PUBLICATIONS

Angiolink, The Expanding Vascular Staple [brochure], 1 page total.

(Continued)

*Primary Examiner*—Julian W Woo
(74) *Attorney, Agent, or Firm*—Levine Bagade Han LLP; Charles C. Fowler, Esq.

(57) ABSTRACT

Apparatus and methods are provided for forming a gastrointestinal tissue fold by engaging tissue at a first tissue contact point, moving the first tissue contact point from a position initially distal to a second tissue contact point to a position proximal of the second contact point to form a tissue fold, and extending an anchor assembly through the tissue fold near the second tissue contact point. Adjustable anchor assemblies, as well as anchor delivery systems, are also provided.

3 Claims, 19 Drawing Sheets

U.S. PATENT DOCUMENTS

| | | |
|---|---|---|
| 3,664,345 A | 5/1972 | Dabbs et al. |
| 3,753,438 A | 8/1973 | Wood et al. |
| 3,867,944 A | 2/1975 | Samuels |
| 3,874,388 A | 4/1975 | King et al. |
| 3,910,281 A | 10/1975 | Kletschka et al. |
| 3,976,079 A | 8/1976 | Samuels et al. |
| 4,007,743 A | 2/1977 | Blake |
| 4,060,089 A | 11/1977 | Noiles |
| 4,069,825 A | 1/1978 | Akiyama |
| 4,235,238 A * | 11/1980 | Ogiu et al. .................. 606/145 |
| 4,245,624 A | 1/1981 | Komiya |
| 4,367,746 A | 1/1983 | Derechinsky |
| 4,414,720 A | 11/1983 | Crooms |
| 4,462,402 A | 7/1984 | Burgio |
| 4,494,531 A | 1/1985 | Gianturco |
| 4,532,926 A | 8/1985 | O'Holla |
| 4,534,350 A | 8/1985 | Golden et al. |
| 4,548,202 A | 10/1985 | Duncan |
| 4,586,503 A | 5/1986 | Kirsh et al. |
| 4,592,339 A | 6/1986 | Kumak et al. |
| 4,592,356 A | 6/1986 | Gutierrez |
| 4,595,007 A | 6/1986 | Mericle |
| 4,610,250 A | 9/1986 | Green |
| 4,669,473 A | 6/1987 | Richards et al. |
| 4,705,040 A | 11/1987 | Mueller et al. |
| 4,711,002 A | 12/1987 | Kreeger |
| 4,724,840 A | 2/1988 | McVay et al. |
| 4,750,492 A | 6/1988 | Jacobs et al. |
| 4,765,335 A | 8/1988 | Schmidt et al. |
| 4,832,055 A | 5/1989 | Palestrant |
| 4,841,888 A | 6/1989 | Mills et al. |
| 4,873,976 A | 10/1989 | Schreiber |
| 4,890,615 A | 1/1990 | Caspari et al. |
| 4,923,461 A | 5/1990 | Caspari et al. |
| 4,929,240 A | 5/1990 | Kirsh et al. |
| 4,957,498 A | 9/1990 | Caspari et al. |
| 5,032,127 A | 7/1991 | Frazee et al. |
| 5,035,692 A | 7/1991 | Lyon et al. |
| 5,037,433 A | 8/1991 | Wilk et al. |
| 5,041,129 A | 8/1991 | Hayhurst et al. |
| 5,059,201 A | 10/1991 | Asnis |
| 5,073,166 A | 12/1991 | Parks et al. |
| 5,088,979 A | 2/1992 | Filipi et al. |
| 5,100,418 A | 3/1992 | Yoon et al. |
| 5,108,420 A | 4/1992 | Marks |
| 5,122,136 A | 6/1992 | Gugliemi et al. |
| 5,123,914 A | 6/1992 | Cope |
| RE34,021 E | 8/1992 | Mueller et al. |
| 5,201,746 A | 4/1993 | Shichman |
| 5,203,864 A | 4/1993 | Phillips |
| 5,217,471 A | 6/1993 | Burkhart |
| 5,217,473 A | 6/1993 | Yoon |
| 5,222,508 A | 6/1993 | Contarini |
| 5,222,961 A | 6/1993 | Nakao et al. |
| 5,222,963 A | 6/1993 | Brinkerhoff et al. |
| 5,224,946 A | 7/1993 | Hayhurst et al. |
| 5,234,430 A | 8/1993 | Huebner |
| 5,234,445 A | 8/1993 | Walker et al. |
| 5,250,053 A | 10/1993 | Snyder |
| 5,254,126 A | 10/1993 | Filipi et al. |
| 5,261,916 A | 11/1993 | Engelson |
| 5,268,001 A | 12/1993 | Nicholson et al. |
| 5,269,809 A * | 12/1993 | Hayhurst et al. ............ 606/232 |
| 5,282,827 A | 2/1994 | Kensey et al. |
| 5,284,488 A | 2/1994 | Sideris |
| 5,304,184 A | 4/1994 | Hathaway et al. |
| 5,304,195 A | 4/1994 | Twyford, Jr. et al. |
| 5,304,204 A | 4/1994 | Bregen |
| 5,316,543 A | 5/1994 | Eberbach |
| 5,327,914 A | 7/1994 | Shlain |
| 5,330,503 A | 7/1994 | Yoon |
| 5,334,217 A | 8/1994 | Das |
| 5,342,376 A | 8/1994 | Ruff |
| 5,345,949 A | 9/1994 | Shlain |
| 5,354,298 A | 10/1994 | Lee et al. |
| 5,366,459 A | 11/1994 | Yoon |
| 5,366,479 A | 11/1994 | McGarry et al. |
| 5,372,146 A | 12/1994 | Branch |
| 5,372,604 A | 12/1994 | Trott |
| 5,374,275 A | 12/1994 | Bradley et al. |
| 5,380,334 A | 1/1995 | Torrie et al. |
| 5,382,231 A | 1/1995 | Shlain |
| 5,395,030 A | 3/1995 | Kuramoto et al. |
| 5,403,326 A | 4/1995 | Harrison et al. |
| 5,403,329 A | 4/1995 | Hinchcliffe |
| 5,417,691 A | 5/1995 | Hayhurst et al. |
| 5,417,699 A | 5/1995 | Klein et al. |
| 5,425,744 A | 6/1995 | Fagan et al. |
| 5,429,598 A | 7/1995 | Waxman et al. |
| 5,431,666 A | 7/1995 | Sauer et al. |
| 5,433,721 A | 7/1995 | Hooven et al. |
| 5,433,727 A | 7/1995 | Sideris |
| 5,437,680 A | 8/1995 | Yoon |
| 5,437,681 A | 8/1995 | Meade et al. |
| 5,445,167 A | 8/1995 | Yoon et al. |
| 5,458,609 A | 10/1995 | Gordon et al. |
| 5,462,560 A | 10/1995 | Stevens |
| 5,462,561 A | 10/1995 | Voda |
| 5,465,894 A | 11/1995 | Clark et al. |
| 5,470,337 A | 11/1995 | Moss |
| 5,470,338 A | 11/1995 | Whitfield et al. |
| 5,476,470 A | 12/1995 | Fitzgibbons, Jr. |
| 5,478,354 A | 12/1995 | Tovey et al. |
| 5,480,405 A | 1/1996 | Yoon |
| 5,496,332 A | 3/1996 | Sierra et al. |
| 5,496,334 A | 3/1996 | Klundt et al. |
| 5,499,991 A | 3/1996 | Garman et al. |
| 5,501,691 A | 3/1996 | Goldrath |
| 5,507,811 A | 4/1996 | Koike et al. |
| 5,520,691 A | 5/1996 | Branch |
| 5,520,701 A | 5/1996 | Lerch |
| 5,522,843 A | 6/1996 | Zang |
| 5,527,321 A | 6/1996 | Hinchliffe |
| 5,527,322 A | 6/1996 | Klein et al. |
| 5,527,342 A | 6/1996 | Pietrzak et al. |
| 5,531,759 A | 7/1996 | Kensey et al. |
| 5,531,788 A | 7/1996 | Dibie et al. |
| 5,540,704 A | 7/1996 | Gordon et al. |
| 5,545,178 A * | 8/1996 | Kensey et al. ............... 606/213 |
| 5,549,621 A | 8/1996 | Bessler et al. |
| 5,562,684 A | 10/1996 | Kammerer |
| 5,562,686 A | 10/1996 | Sauer et al. |
| 5,562,688 A | 10/1996 | Riza |
| 5,569,274 A | 10/1996 | Rapacki et al. |
| 5,569,306 A | 10/1996 | Thal |
| 5,571,116 A | 11/1996 | Bolanos et al. |
| 5,571,119 A | 11/1996 | Atala |
| 5,573,540 A | 11/1996 | Yoon |
| 5,573,548 A | 11/1996 | Nazre et al. |
| 5,578,045 A | 11/1996 | Das |
| 5,582,616 A | 12/1996 | Bolduc et al. |
| 5,584,835 A | 12/1996 | Greenfield |
| 5,584,859 A | 12/1996 | Brotz |
| 5,601,557 A | 2/1997 | Hayhurst |
| 5,603,718 A | 2/1997 | Xu |
| 5,613,974 A | 3/1997 | Andreas et al. |
| 5,613,975 A | 3/1997 | Christy |
| 5,626,588 A | 5/1997 | Sauer et al. |
| 5,626,614 A | 5/1997 | Hart |
| 5,630,540 A | 5/1997 | Blewett |
| 5,632,752 A | 5/1997 | Buelna |
| 5,643,274 A | 7/1997 | Sander et al. |
| 5,643,295 A | 7/1997 | Yoon |
| 5,643,317 A | 7/1997 | Pavcnik et al. |

| | | | | | | |
|---|---|---|---|---|---|---|
| 5,643,320 A | 7/1997 | Lower et al. | | 5,964,765 A | 10/1999 | Fenton, Jr. et al. |
| 5,658,312 A | 8/1997 | Green et al. | | 5,964,782 A | 10/1999 | Lafontaine et al. |
| 5,658,313 A | 8/1997 | Thal | | 5,964,783 A | 10/1999 | Grafton et al. |
| 5,662,662 A | 9/1997 | Bishop et al. | | 5,976,127 A | 11/1999 | Lax |
| 5,662,663 A | 9/1997 | Shallman | | 5,976,158 A | 11/1999 | Adams et al. |
| 5,665,109 A | 9/1997 | Yoon | | 5,976,159 A | 11/1999 | Bolduc et al. |
| 5,665,112 A | 9/1997 | Thal | | 5,980,558 A | 11/1999 | Wiley |
| 5,667,513 A | 9/1997 | Torrie et al. | | 5,984,933 A | 11/1999 | Yoon |
| 5,679,005 A | 10/1997 | Einstein | | 5,993,476 A | 11/1999 | Groiso |
| 5,683,417 A | 11/1997 | Cooper | | 6,013,083 A | 1/2000 | Bennett |
| 5,683,419 A | 11/1997 | Thal | | 6,017,358 A | 1/2000 | Yoon et al. |
| 5,690,655 A | 11/1997 | Hart et al. | | 6,027,523 A | 2/2000 | Schmieding |
| 5,693,060 A | 12/1997 | Martin | | 6,033,430 A | 3/2000 | Bonutti |
| 5,700,273 A | 12/1997 | Buelna et al. | | 6,045,497 A | 4/2000 | Schweich, Jr. et al. |
| 5,702,421 A | 12/1997 | Schneidt | | 6,045,573 A | 4/2000 | Wenstrom, Jr. et al. |
| 5,707,394 A | 1/1998 | Miller et al. | | 6,050,936 A | 4/2000 | Schweich, Jr. et al. |
| 5,709,708 A | 1/1998 | Thal | | 6,053,935 A | 4/2000 | Brenneman et al. |
| 5,713,903 A | 2/1998 | Sander et al. | | 6,056,770 A | 5/2000 | Epstein et al. |
| 5,720,765 A | 2/1998 | Thal | | 6,059,715 A | 5/2000 | Schweich, Jr. et al. |
| 5,724,978 A | 3/1998 | Tenhoff | | 6,059,719 A | 5/2000 | Yamamoto et al. |
| 5,725,552 A | 3/1998 | Kotula et al. | | 6,074,401 A | 6/2000 | Gardiner et al. |
| 5,732,707 A | 3/1998 | Widder et al. | | 6,077,214 A | 6/2000 | Mortier et al. |
| 5,741,297 A | 4/1998 | Simon | | 6,077,281 A | 6/2000 | Das |
| 5,749,893 A | 5/1998 | Vidal et al. | | 6,077,291 A | 6/2000 | Das |
| 5,752,963 A | 5/1998 | Allard et al. | | 6,079,414 A | 6/2000 | Roth et al. |
| 5,766,189 A | 6/1998 | Matsuno | | 6,086,600 A | 7/2000 | Kortenbach |
| 5,779,719 A | 7/1998 | Klein et al. | | 6,086,601 A | 7/2000 | Yoon |
| 5,782,859 A | 7/1998 | Nicholas et al. | | 6,110,183 A | 8/2000 | Cope |
| 5,782,865 A | 7/1998 | Grotz | | 6,113,609 A | 9/2000 | Adams |
| 5,787,897 A | 8/1998 | Kieturakis | | 6,113,611 A | 9/2000 | Allen et al. |
| 5,792,152 A | 8/1998 | Klein et al. | | 6,119,913 A | 9/2000 | Adams et al. |
| 5,792,153 A | 8/1998 | Swain et al. | | 6,149,658 A | 11/2000 | Gardiner et al. |
| 5,797,929 A | 8/1998 | Andreas et al. | | 6,152,935 A | 11/2000 | Kammerer et al. |
| 5,797,960 A | 8/1998 | Stevens et al. | | 6,159,146 A | 12/2000 | El Gazayerli |
| 5,810,849 A | 9/1998 | Kontos | | 6,162,168 A | 12/2000 | Schweich, Jr. et al. |
| 5,810,851 A | 9/1998 | Yoon | | 6,165,119 A | 12/2000 | Schweich, Jr. et al. |
| 5,810,853 A | 9/1998 | Yoon | | 6,165,120 A | 12/2000 | Schweich, Jr. et al. |
| 5,814,064 A | 9/1998 | Daniel et al. | | 6,167,889 B1 | 1/2001 | Benetti |
| 5,814,070 A | 9/1998 | Borzone et al. | | 6,171,320 B1 | 1/2001 | Monassevitch |
| 5,817,110 A | 10/1998 | Kronner | | 6,174,323 B1 | 1/2001 | Biggs et al. |
| 5,823,956 A | 10/1998 | Roth et al. | | 6,179,195 B1 | 1/2001 | Adams et al. |
| 5,824,011 A | 10/1998 | Stone et al. | | 6,183,411 B1 | 2/2001 | Mortier et al. |
| 5,827,298 A | 10/1998 | Hart et al. | | RE37,117 E | 3/2001 | Palermo |
| 5,829,447 A | 11/1998 | Stevens et al. | | 6,197,022 B1 | 3/2001 | Baker |
| 5,836,955 A | 11/1998 | Buelna et al. | | 6,214,007 B1 | 4/2001 | Anderson |
| 5,840,078 A | 11/1998 | Yerys | | 6,231,561 B1 | 5/2001 | Frazier et al. |
| 5,843,084 A | 12/1998 | Hart et al. | | 6,238,412 B1 | 5/2001 | Dubrul et al. |
| 5,843,126 A | 12/1998 | Jameel | | 6,245,079 B1 | 6/2001 | Nobles et al. |
| 5,846,261 A | 12/1998 | Kotula et al. | | 6,260,552 B1 | 7/2001 | Mortier et al. |
| 5,855,614 A | 1/1999 | Stevens et al. | | 6,261,222 B1 | 7/2001 | Schweich, Jr. et al. |
| 5,860,991 A | 1/1999 | Klein et al. | | 6,264,602 B1 | 7/2001 | Mortier et al. |
| 5,861,003 A | 1/1999 | Latson et al. | | 6,270,515 B1 | 8/2001 | Linden et al. |
| 5,868,762 A | 2/1999 | Cragg et al. | | 6,283,973 B1 | 9/2001 | Hubbard et al. |
| 5,879,371 A | 3/1999 | Gardiner et al. | | 6,290,674 B1 | 9/2001 | Roue et al. |
| 5,887,594 A | 3/1999 | LoCiero, III | | 6,293,956 B1 | 9/2001 | Crainich et al. |
| 5,888,247 A | 3/1999 | Benetti | | 6,296,656 B1 | 10/2001 | Bolduc et al. |
| 5,891,168 A | 4/1999 | Thal | | 6,306,159 B1 | 10/2001 | Schwartz et al. |
| 5,893,856 A | 4/1999 | Jacobs et al. | | 6,306,163 B1 | 10/2001 | Fitz |
| 5,895,404 A | 4/1999 | Ruiz | | 6,312,437 B1 | 11/2001 | Kortenbach |
| 5,897,562 A | 4/1999 | Bolanos et al. | | 6,315,789 B1 | 11/2001 | Cragg |
| 5,899,920 A | 5/1999 | DeSatnick et al. | | 6,322,563 B1 | 11/2001 | Cummings et al. |
| 5,899,921 A | 5/1999 | Caspari et al. | | 6,322,580 B1 | 11/2001 | Kanner |
| 5,901,895 A | 5/1999 | Heaton et al. | | 6,332,468 B1 | 12/2001 | Benetti |
| 5,916,224 A | 6/1999 | Esplin | | 6,332,863 B1 | 12/2001 | Schweich, Jr. et al. |
| 5,925,059 A | 7/1999 | Palermo et al. | | 6,332,864 B1 | 12/2001 | Schweich, Jr. et al. |
| 5,928,264 A | 7/1999 | Sugarbaker et al. | | 6,332,893 B1 | 12/2001 | Mortier et al. |
| 5,944,738 A | 8/1999 | Amplatz et al. | | 6,336,940 B1 | 1/2002 | Graf et al. |
| 5,947,983 A | 9/1999 | Solar et al. | | 6,346,074 B1 | 2/2002 | Roth |
| 5,947,997 A | 9/1999 | Pavcnik et al. | | 6,348,064 B1 | 2/2002 | Kanner |
| 5,948,001 A | 9/1999 | Larsen | | 6,352,503 B1 * | 3/2002 | Matsui et al. ............... 600/104 |
| 5,954,731 A | 9/1999 | Yoon | | 6,355,052 B1 | 3/2002 | Neuss et al. |
| 5,954,732 A | 9/1999 | Hart et al. | | 6,358,197 B1 | 3/2002 | Silverman et al. |
| 5,961,440 A | 10/1999 | Schweich, Jr. et al. | | 6,363,938 B2 | 4/2002 | Saadat et al. |

| | | |
|---|---|---|
| 6,368,339 B1 | 4/2002 | Amplatz et al. |
| 6,387,104 B1 | 5/2002 | Pugsley, Jr. |
| 6,391,044 B1 | 5/2002 | Yadav et al. |
| 6,402,679 B1 | 6/2002 | Mortier et al. |
| 6,402,680 B2 | 6/2002 | Mortier et al. |
| 6,406,420 B1 | 6/2002 | McCarthy et al. |
| H2037 H | 7/2002 | Yates et al. |
| 6,423,087 B1 | 7/2002 | Sawada |
| 6,425,911 B1 | 7/2002 | Akerfeldt et al. |
| 6,447,533 B1 | 9/2002 | Adams et al. |
| 6,494,888 B1 | 12/2002 | Laufer et al. |
| 6,506,196 B1 | 1/2003 | Laufer |
| 6,533,796 B1 | 3/2003 | Sauer et al. |
| 6,537,285 B1 | 3/2003 | Hatasaka, Jr. et al. |
| 6,554,845 B1 | 4/2003 | Fleenor et al. |
| 6,558,400 B2 | 5/2003 | Deem et al. |
| 6,572,629 B2 | 6/2003 | Kalloo et al. |
| 6,641,592 B1 | 11/2003 | Sauer et al. |
| 6,656,194 B1 | 12/2003 | Gannoe et al. |
| 6,663,639 B1 | 12/2003 | Laufer et al. |
| 6,669,707 B1 * | 12/2003 | Swanstrom et al. ......... 606/153 |
| 6,695,764 B2 | 2/2004 | Silverman et al. |
| 6,699,263 B2 * | 3/2004 | Cope ......................... 606/232 |
| 6,716,232 B1 | 4/2004 | Vidal et al. |
| 6,719,763 B2 | 4/2004 | Chung et al. |
| 6,719,764 B1 | 4/2004 | Gellman et al. |
| 6,736,828 B1 | 5/2004 | Adams et al. |
| 6,746,460 B2 | 6/2004 | Gannoe et al. |
| 6,755,843 B2 | 6/2004 | Chung et al. |
| 6,773,440 B2 | 8/2004 | Gannoe et al. |
| 6,773,441 B1 | 8/2004 | Laufer et al. |
| 6,821,285 B2 | 11/2004 | Laufer et al. |
| 6,835,199 B2 | 12/2004 | McGuckin, Jr. et al. |
| 2001/0016675 A1 | 8/2001 | Mortier et al. |
| 2001/0025171 A1 | 9/2001 | Mortier et al. |
| 2001/0049509 A1 | 12/2001 | Sekine et al. |
| 2001/0051815 A1 | 12/2001 | Esplin |
| 2001/0056282 A1 | 12/2001 | Sonnenschein et al. |
| 2002/0010490 A1 | 1/2002 | Schaller et al. |
| 2002/0013608 A1 | 1/2002 | ElAttrache et al. |
| 2002/0019649 A1 | 2/2002 | Sikora et al. |
| 2002/0022851 A1 | 2/2002 | Kalloo et al. |
| 2002/0029080 A1 | 3/2002 | Mortier et al. |
| 2002/0040226 A1 | 4/2002 | Laufer et al. |
| 2002/0055757 A1 | 5/2002 | Torre et al. |
| 2002/0058855 A1 | 5/2002 | Schweich, Jr. et al. |
| 2002/0065534 A1 | 5/2002 | Hermann et al. |
| 2002/0068849 A1 | 6/2002 | Schweich, Jr. et al. |
| 2002/0068945 A1 | 6/2002 | Sixto, Jr. et al. |
| 2002/0072761 A1 | 6/2002 | Abrams et al. |
| 2002/0077524 A1 | 6/2002 | Schweich, Jr. et al. |
| 2002/0078967 A1 | 6/2002 | Sixto, Jr. et al. |
| 2002/0082621 A1 | 6/2002 | Schurr et al. |
| 2002/0082622 A1 | 6/2002 | Kane |
| 2002/0107530 A1 | 8/2002 | Sauer et al. |
| 2002/0183768 A1 | 12/2002 | Deem et al. |
| 2002/0193816 A1 | 12/2002 | Laufer et al. |
| 2003/0009085 A1 | 1/2003 | Arai et al. |
| 2003/0055442 A1 | 3/2003 | Laufer et al. |
| 2003/0065359 A1 | 4/2003 | Weller et al. |
| 2003/0109892 A1 | 6/2003 | Deem et al. |
| 2003/0139752 A1 | 7/2003 | Pasricha et al. |
| 2003/0158582 A1 | 8/2003 | Bonutti et al. |
| 2003/0167062 A1 | 9/2003 | Gambale et al. |
| 2003/0167651 A1 | 9/2003 | Page et al. |
| 2003/0171760 A1 | 9/2003 | Gambale |
| 2003/0176890 A1 | 9/2003 | Buckman et al. |
| 2003/0181924 A1 | 9/2003 | Yamamoto et al. |
| 2003/0204205 A1 | 10/2003 | Sauer et al. |
| 2003/0240205 | 10/2003 | Sauer et al. |
| 2003/0208209 A1 | 11/2003 | Gambale et al. |
| 2003/0216613 A1 | 11/2003 | Suzuki et al. |
| 2003/0225312 A1 | 12/2003 | Suzuki et al. |
| 2003/0229296 A1 | 12/2003 | Ishikawa et al. |
| 2003/0236536 A1 | 12/2003 | Grigoryants et al. |
| 2004/0010271 A1 | 1/2004 | Kortenbach |
| 2004/0030347 A1 | 2/2004 | Gannoe et al. |
| 2004/0049095 A1 | 3/2004 | Goto et al. |
| 2004/0059346 A1 | 3/2004 | Adams et al. |
| 2004/0082963 A1 | 4/2004 | Gannoe et al. |
| 2004/0088008 A1 | 5/2004 | Gannoe et al. |
| 2004/0092974 A1 | 5/2004 | Gannoe et al. |
| 2004/0093091 A1 | 5/2004 | Gannoe et al. |
| 2004/0122452 A1 | 6/2004 | Deem et al. |
| 2004/0122453 A1 | 6/2004 | Deem et al. |
| 2004/0122474 A1 | 6/2004 | Gellman et al. |
| 2004/0138682 A1 | 7/2004 | Onuki et al. |
| 2004/0147941 A1 | 7/2004 | Takemoto |
| 2004/0176784 A1 | 9/2004 | Okada |
| 2004/0193117 A1 | 9/2004 | Laufer et al. |
| 2004/0193184 A1 | 9/2004 | Laufer et al. |
| 2004/0193193 A1 | 9/2004 | Laufer et al. |
| 2004/0193194 A1 | 9/2004 | Laufer et al. |
| 2004/0194790 A1 | 10/2004 | Laufer et al. |
| 2004/0215216 A1 | 10/2004 | Gannoe et al. |
| 2004/0243152 A1 | 12/2004 | Taylor et al. |
| 2004/0249362 A1 | 12/2004 | Levine et al. |
| 2004/0249392 A1 | 12/2004 | Mikkaichi et al. |
| 2004/0249395 A1 | 12/2004 | Mikkaichi et al. |
| 2005/0033320 A1 | 2/2005 | McGuckin, Jr. et al. |
| 2005/0033328 A1 | 2/2005 | Laufer et al. |
| 2005/0043758 A1 | 2/2005 | Golden et al. |
| 2005/0049617 A1 | 3/2005 | Chatlynne et al. |

FOREIGN PATENT DOCUMENTS

| | | |
|---|---|---|
| EP | 0 847 727 A1 | 6/1998 |
| EP | 1 031 321 A1 | 8/2000 |
| FR | 2 768 324 A1 | 3/1999 |
| GB | 2 165 559 A | 4/1986 |
| WO | WO 92/04870 A1 | 4/1992 |
| WO | WO 95/19140 A1 | 7/1995 |
| WO | WO 95/25468 A1 | 9/1995 |
| WO | WO 99/22649 A2 | 5/1999 |
| WO | WO 00/40159 A1 | 7/2000 |
| WO | WO 00/57796 A1 | 10/2000 |
| WO | WO 00/78227 A1 | 12/2000 |
| WO | WO 00/78229 A1 | 12/2000 |
| WO | WO 01/21246 A1 | 3/2001 |
| WO | WO 01/66001 A2 | 9/2001 |
| WO | WO 01/66018 A1 | 9/2001 |
| WO | WO 01/85034 A1 | 11/2001 |
| WO | WO 01/87144 A1 | 11/2001 |
| WO | WO 01/89370 A2 | 11/2001 |
| WO | WO 01/89392 A2 | 11/2001 |
| WO | WO 01/89393 A1 | 11/2001 |
| WO | WO 02/00119 A2 | 1/2002 |
| WO | WO 02/24080 A2 | 3/2002 |
| WO | WO 02/39880 A2 | 5/2002 |
| WO | WO 02/060328 A1 | 8/2002 |
| WO | WO 02/064012 A2 | 8/2002 |
| WO | WO 02/085252 A1 | 10/2002 |
| WO | WO 02/094105 A2 | 11/2002 |
| WO | WO 03/007796 A2 | 1/2003 |
| WO | WO 03/007799 A2 | 1/2003 |
| WO | WO 03/090633 A2 | 11/2003 |
| WO | WO 03/092509 A1 | 11/2003 |
| WO | WO 03/094785 A1 | 11/2003 |
| WO | WO 03/096909 A1 | 11/2003 |
| WO | WO 03/099137 A2 | 12/2003 |
| WO | WO 2004/004542 A2 | 1/2004 |
| WO | WO 2004/004544 A2 | 1/2004 |
| WO | WO 2004/019787 A2 | 3/2004 |
| WO | WO 2004/019788 A2 | 3/2004 |
| WO | WO 2004/021865 A2 | 3/2004 |
| WO | WO 2004/021867 A2 | 3/2004 |

| | | | |
|---|---|---|---|
| WO | WO 2004/021868 A2 | 3/2004 |
| WO | WO 2004/021873 A2 | 3/2004 |
| WO | WO 2004/021894 A1 | 3/2004 |
| WO | WO 2004/056273 A1 | 7/2004 |
| WO | WO 2004/075787 A1 | 9/2004 |
| WO | WO 2005/004727 A1 | 1/2005 |
| WO | WO 2005/037152 A1 | 4/2005 |

OTHER PUBLICATIONS

Bluett et al., "Experimental Evaluation of Staple Lines in Gastric Surgery," *Arch. Surg.*, vol. 122, (Jul. 1987), pp. 772-776.

Brolin et al., Experimental Evaluation of Techniques of Gastric Paritioning for Morbid Obesity, Surgery, Gynecology & Obstetrics, vol. 153, (Dec. 1981), pp. 878-882.

Johnston et al. "The Magenstrasse and Mill Operation of Morbid Obesity", *Obesity Surgery* 13, (2003), pp. 10-16.

Okudaira et al., "The Healing and Tensile Strength of the Gastroplasty Staple Line," *The American Surgeon*, (Oct. 1984), pp. 564-568.

Surgical Dynamics Inc., The S•D•sorb Meniscal Stapler [brochure] (1997), 3 pages total.

Sutura, The Next Generation in Vascular Suturing Devices: SuperStitch [brochure], 2 pages total.

Chuttani et al., "A Novel Endoscopic Full-thickness Plicator for Treatment of GERD: An Animal Model Study," *Gastrointestinal Endoscopy*, vol. 26, No. 1,(2002), pp. 116-122.

\* cited by examiner

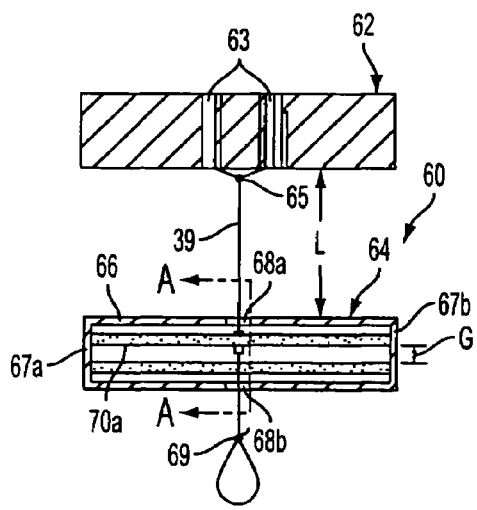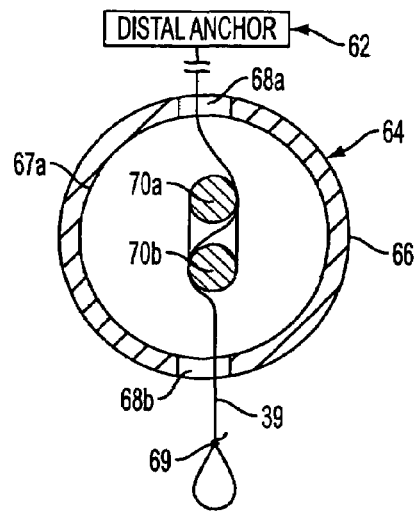
FIG. 7A
FIG. 7C
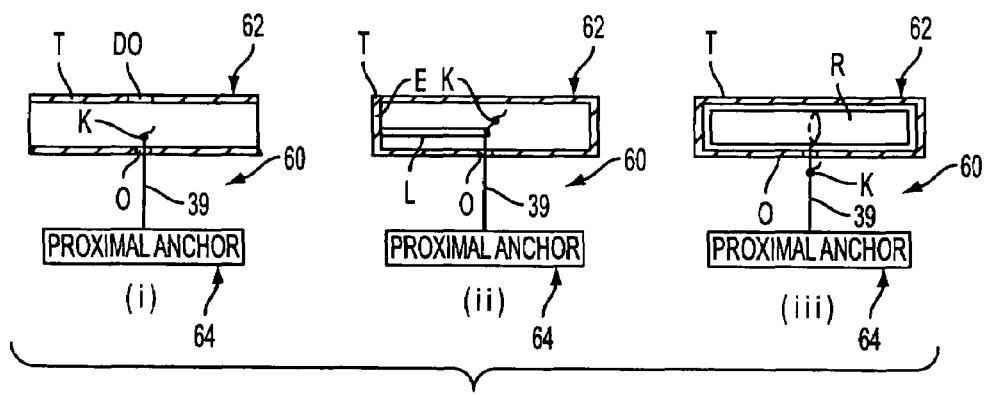
FIG. 7B

APPARATUS AND METHODS FOR FORMING AND SECURING GASTROINTESTINAL TISSUE FOLDS

REFERENCE TO RELATED APPLICATIONS

This application claims priority from U.S. provisional patent application Ser. No. 60/500,627, filed Sep. 5, 2003, and is a Continuation-In-Part of U.S. patent application Ser. No. 10/612,170, filed Jul. 1, 2003, as well as U.S. patent application Ser. No. 10/639,162, filed Aug. 11, 2003, both of which claim priority from U.S. provisional patent application Ser. No. 60/433,065, filed Dec. 11, 2002, all of which are incorporated herein by reference in their entirety.

FIELD OF THE INVENTION

The present invention relates to methods and apparatus for intraluminally forming and securing gastrointestinal ("GI") tissue folds. More particularly, the present invention relates to methods and apparatus for reducing the effective cross-sectional area of a gastrointestinal lumen.

BACKGROUND OF THE INVENTION

Morbid obesity is a serious medical condition pervasive in the United States and other countries. Its complications include hypertension, diabetes, coronary artery disease, stroke, congestive heart failure, multiple orthopedic problems and pulmonary insufficiency with markedly decreased life expectancy.

Several surgical techniques have been developed to treat morbid obesity, e.g., bypassing an absorptive surface of the small intestine, or reducing the stomach size. These procedures are difficult to perform in morbidly obese patients because it is often difficult to gain access to the digestive organs. In particular, the layers of fat encountered in morbidly obese patients make difficult direct exposure of the digestive organs with a wound retractor, and standard laparoscopic trocars may be of inadequate length.

In addition, previously known open surgical procedures may present numerous life-threatening postoperative complications, and may cause a typical diarrhea, electrolytic imbalance, unpredictable weight loss and reflux of nutritious chyme proximal to the site of the anastamosis. Further, the sutures or staples that are often used in these surgical procedures may require extensive training by the clinician to achieve competent use, and may concentrate significant force over a small surface area of the tissue, thereby potentially causing the suture or staple to tear through the tissue.

The gastrointestinal lumen includes four tissue layers, wherein the mucosa layer is the top tissue layer followed by connective tissue, the muscularis layer and the serosa layer. One problem with conventional gastrointestinal reduction systems is that the anchors (or staples) must engage at least the muscularis tissue layer in order to provide a proper foundation. In other words, the mucosa and connective tissue layers typically are not strong enough to sustain the tensile loads imposed by normal movement of the stomach wall during ingestion and processing of food. In particular, these layers tend to stretch elastically rather than firmly hold the anchors (or staples) in position, and accordingly, the more rigid muscularis and/or serosa layer must be engaged. This problem of capturing the muscularis or serosa layers becomes particularly acute where it is desired to place an anchor or other apparatus transesophageally rather than intraoperatively, since care must be taken in piercing the tough stomach wall not to inadvertently puncture adjacent tissue or organs.

In view of the aforementioned limitations, it would be desirable to provide methods and apparatus for forming gastrointestinal tissue folds that achieve gastric reduction by reconfiguring the GI lumen of a patient.

It would be desirable to provide methods and apparatus for forming gastrointestinal tissue folds using anchors that can be reconfigured from a reduced delivery profile to an expanded deployed profile.

It also would be desirable to provide methods and apparatus for forming gastrointestinal tissue folds, wherein an anchor assembly is extended across stomach folds that include the muscularis and serosa tissue layers.

It further would be desirable to provide methods and apparatus for forming gastrointestinal tissue folds, wherein the anchor assembly is deployed in a manner that reduces a possibility of injuring neighboring organs.

It still further would be desirable to provide methods and apparatus for forming gastrointestinal tissue folds, wherein reduced training of a clinician is required to achieve competent use of the anchor assembly.

SUMMARY OF THE INVENTION

In view of the foregoing, it is an object of the present invention to provide methods and apparatus for forming gastrointestinal tissue folds that achieve gastric reduction by reconfiguring the GI lumen of a patient.

It is another object of the present invention to provide methods and apparatus for forming gastrointestinal tissue folds using anchors that can be reconfigured from a reduced delivery profile to an expanded deployed profile.

It is an additional object of this invention to provide methods and apparatus for forming gastrointestinal tissue folds in which an anchor assembly is extended across stomach folds that include the muscularis and serosa tissue layers.

It is a further object of the present invention to provide methods and apparatus for forming gastrointestinal tissue folds, wherein the anchor assembly is deployed in a manner that reduces a possibility of injuring neighboring organs.

It is yet another object to provide methods and apparatus for forming gastrointestinal tissue folds, wherein reduced training of a clinician is required to achieve competent use of the anchor assembly.

These and other objects of the present invention are accomplished by providing a catheter configured for advancement into a patient's gastrointestinal lumen to form a gastrointestinal tissue fold. In one preferred embodiment, the catheter has a distal region including a tissue grabbing assembly adapted to engage and stretch a portion of the tissue wall of the GI lumen at a first tissue contact point. A second tissue contact point is then established with the tissue wall at a location initially proximal of, or in line with, the first tissue contact point. The tissue engaged by the tissue grabbing assembly then is moved to a position proximal of the second tissue contact point to form a tissue fold, and an anchor assembly may be delivered across the tissue fold. Preferably, delivery of the anchor assembly across the tissue fold includes delivering the anchor assembly across the muscularis and serosa layers of the tissue wall.

In a preferred embodiment, the tissue grabbing assembly is carried on a first flexible tube associated with the distal region of the catheter, and the anchor assembly is delivered by an anchor delivery system disposed within a second flexible tube associated with the distal region of the catheter. The tissue grabbing assembly may comprise any of a number of mechanisms configured to engage the tissue wall, including a pair of jaws configured to move between open and closed positions, a plurality of linearly translating barbs, or one or more needles or hooks. The first tissue contact point may be moved from a tissue engagement position distal to, or in line with, the second tissue contact point, to the tissue folding position by any of a number of mechanisms, including a hinge assembly or a treadmill assembly.

More preferably, the distal region of the catheter includes a bendable section that permits the first tissue contact point to be positioned relative to the second tissue contact point so that the tissue fold is oriented substantially perpendicular to the anchor delivery system. In this manner, the anchor delivery system, when deployed, pierces the tissue fold and exits into the interior of the GI lumen, rather than the exterior of the tissue wall, thereby reducing a risk of injury to adjacent organs.

The anchor assembly delivery system of the present invention preferably comprises a needle or obturator adapted to pierce the tissue fold and deliver an anchor assembly. In one preferred embodiment, the anchor assembly comprises a pair of rod-like anchors that are delivered through a needle in a reduced delivery profile, wherein the longitudinal axis of the rods is substantially parallel to the longitudinal axis of the needle. Once ejected from the needle, the rods rotate about 90 degrees to engage the tissue. In other embodiments, the anchor assembly may comprise anchors of various shaped delivered, for example, over the exterior of an obturator.

Methods of using the apparatus of the present invention also are provided.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which:

FIGS. 7A-7C are, respectively, a schematic side-sectional view of a unidirectionally adjustable anchor assembly suitable for use with apparatus of the present invention, schematic side-sectional views of alternative techniques for fixing the distal anchor of the assembly, and a cross-sectional view of the proximal anchor taken along section line A-A of FIG. 7A;

DETAILED DESCRIPTION OF THE INVENTION

In accordance with the principles of the present invention, methods and apparatus are provided for intraluminally forming and securing gastrointestinal ("GI") tissue folds, for example, to reduce the effective cross-sectional area of a GI lumen. These methods and apparatus may be used to treat obesity by approximating the walls of a gastrointestinal lumen to narrow the lumen, thus reducing the area for absorption in the stomach or intestines. More particularly, the present invention involves endoscopic apparatus that engages a tissue wall of the gastrointestinal lumen, creates a tissue fold and disposes an anchor assembly through the tissue fold. Preferably, the anchor assembly is disposed through the muscularis and/or serosa layers of the gastrointestinal lumen. In operation, a distal tip of the probe engages the tissue and then moves the engaged tissue to a proximal position relative to the catheter tip, thereby providing a substantially uniform plication of predetermined size.

Formation of a tissue fold preferably is accomplished using two tissue contact points that are separated by a linear or curvilinear distance, wherein the separation distance between the tissue contact points affects the length and/or depth of the fold. In operation, a tissue grabbing assembly engages the tissue wall in its normal state (i.e., non-folded and substantially flat), thus providing a first tissue contact point. The first tissue contact point then is moved to a position proximal of a second tissue contact point to form the tissue fold. An anchor assembly then may be extended across the tissue fold at the second tissue contact point.

More preferably, the first tissue contact point is used to engage and then stretch or rotate the tissue wall over the second tissue contact point to form the tissue fold. The tissue fold is then articulated to a position so that a portion of the tissue fold overlies the second tissue contact point at an orientation that is substantially normal to the tissue fold. An anchor then is delivered across the tissue fold at or near the second tissue contact point.

Figure 1A:
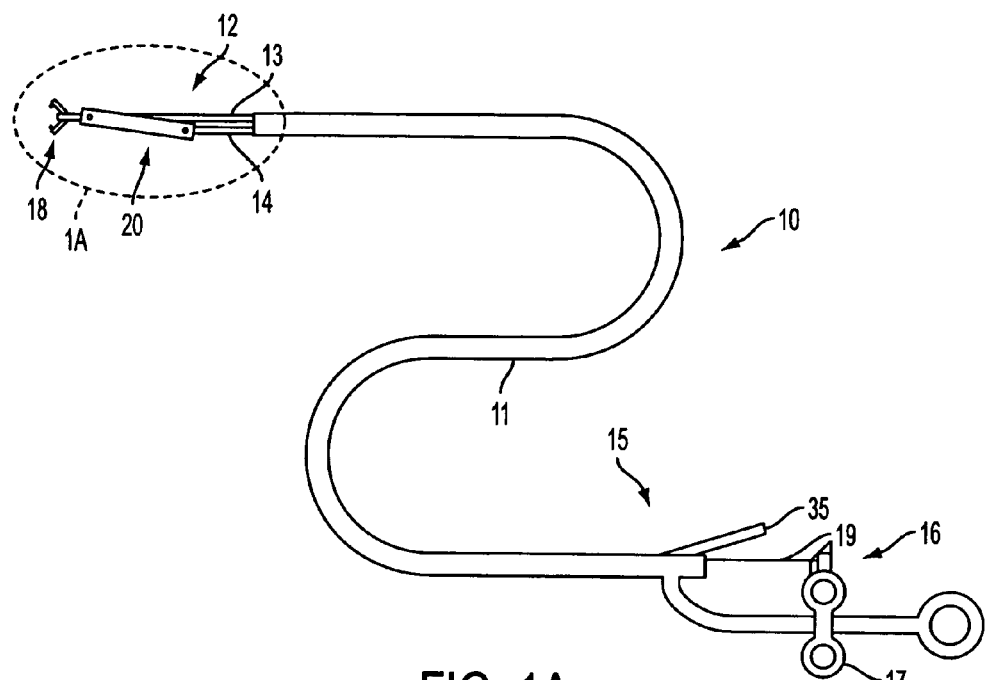
FIGS. 1A and 1B are, respectively, a side view and detail view of apparatus of the present invention for forming a gastrointestinal fold in accordance with the principles of the present invention.

Referring to FIG. 1, apparatus 10 of the present invention comprises torqueable catheter 11 having distal region 12 from which first and second interconnected flexible tubes 13 and 14 extend, and proximal region 15 having handle 16 and actuator 17. Catheter 11 is configured for insertion through a patient's mouth and esophagus into the gastrointestinal lumen. Tissue grabbing assembly 18 is disposed on the distal end of flexible tube 13, and is coupled to actuator 17 via control wire 19 that extends through flexible tube 13.

Figure 1B:
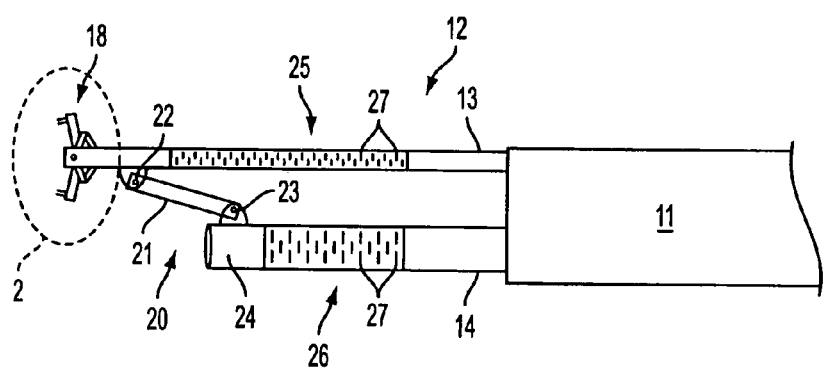

As better illustrated in FIG. 1B, flexible tubes 13 and 14 are connected via hinge assembly 20 that comprises link 21 attached to flexible tube 13 at pivot point 22 and attached to flexible tube 14 at pivot point 23. Hinge assembly 20 prevents tissue grabbing assembly 18 from moving more than a predetermined distance relative to distal end 24 of flexible tube 14.

Still referring to FIG. 1B, flexible tubes 13 and 14 preferably include bendable sections 25 and 26, respectively, that comprise a plurality of through-wall slots 27 to enhance flexibility of the tube. Preferably, flexible tubes 13 and 14 are made from stainless steel with an etched or laser-cut slot pattern. More preferably, the slot pattern is a sinusoidal repeating pattern of slots perpendicular to the longitudinal axis of tubes 13 and 14.

Figure 2A:
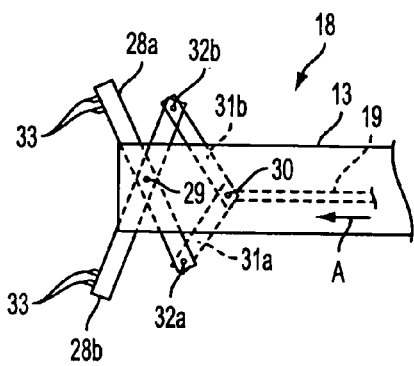
FIGS. 2A and 2B are side-sectional views of a tissue grabbing assembly suitable for use with the apparatus of FIG. 1.
Figure 2B:
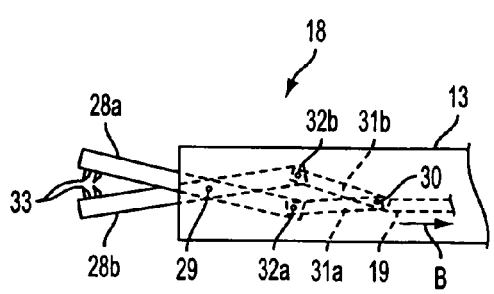

Referring to FIGS. 2A and 2B, tissue grabbing assembly 18 comprises pair of jaws 28a, 28b arranged to rotate about pivot point 29 between an open configuration (FIG. 2A) and a closed configuration (FIG. 2B). Control wire 19 is coupled via pivot point 30 to arms 31a and 31b. Arms 31a and 31b are in turn pivotally coupled to jaws 28a and 28b, respectively, at pivot points 32a and 32b. Each of jaws 28a and 28b preferably includes sharpened teeth 33 disposed near its distal ends to facilitate grasping of the tissue wall of the GI lumen.

Control wire 19 is coupled to actuator 17 of handle 16 so that translation of the wire within flexible tube 13 causes the jaws to open or close. In particular, urging control wire distally (as indicated by arrow A in FIG. 2A) moves pivot point 30 distally, thereby forcing the jaws to open. Urging control wire 19 proximally (as indicated by arrow B in FIG. 2B) moves pivot point 30 proximally, thereby forcing the jaws to close together. In alternative embodiments, tissue grabbing assembly 18 may comprise a grappling hook or fork, or plurality of needles coupled to the distal end of flexible tube 13.

Flexible tube 14 is affixed to and immovable within catheter 11, while flexible tube 13 is coupled to catheter 11 only via hinge 20. Accordingly, when control wire 19 is extended in the distal direction, flexible tube 13 is carried in the distal direction. When control wire 19 is retracted in the proximal direction, flexible tube remains stationary until jaws 28a and 28b close together, after which further retraction of control wire 19 by moving actuator 17 causes flexible tube 13 to buckle in bendable region 25, as described hereinafter.

Figure 3A:
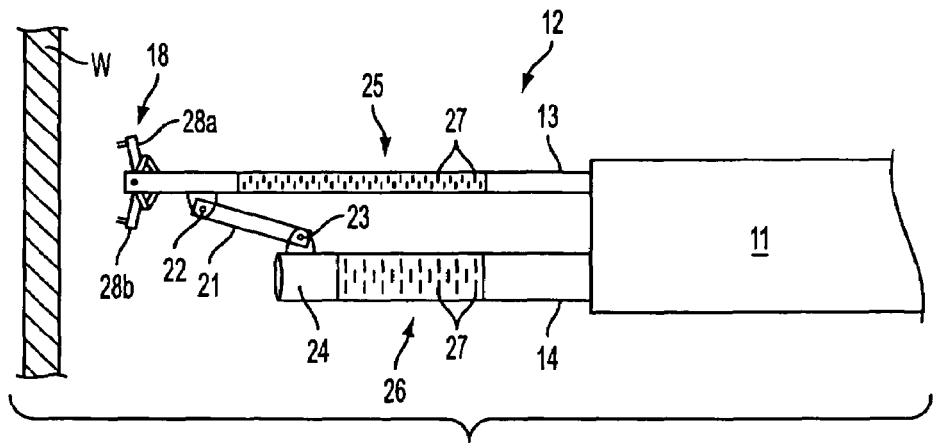
FIGS. 3A-3E are side views illustrating a method of using the apparatus of FIG. 1 to form a gastrointestinal fold.
Figure 3B:
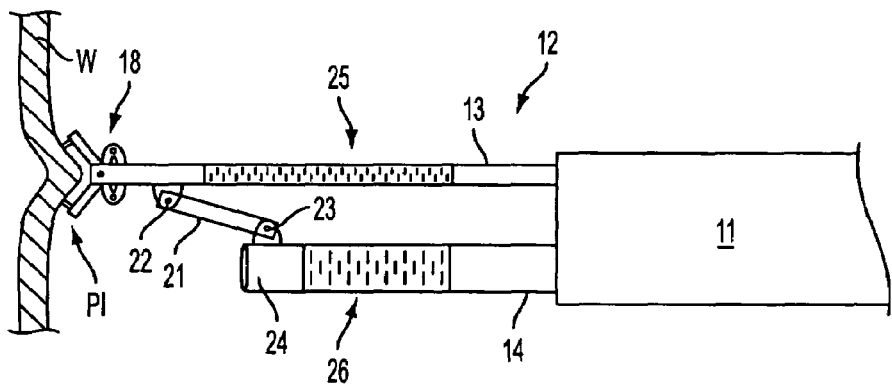

Referring now to FIGS. 1 and 3A-3E, operation of apparatus 10 is described to create a tissue fold in a tissue wall of a GI lumen. In FIG. 3A, distal region 12 of catheter 11 is positioned within a patient's GI lumen transesophageally, and jaws 28a and 28b of tissue grabbing assembly 18 are opened by moving actuator 17 to the distal-most position on handle 16. As depicted in FIG. 3B, actuator 17 may then be moved proximally until the jaws of tissue grabbing assembly 18 engage a portion of tissue wall W at contact point P1.

Figure 3C:
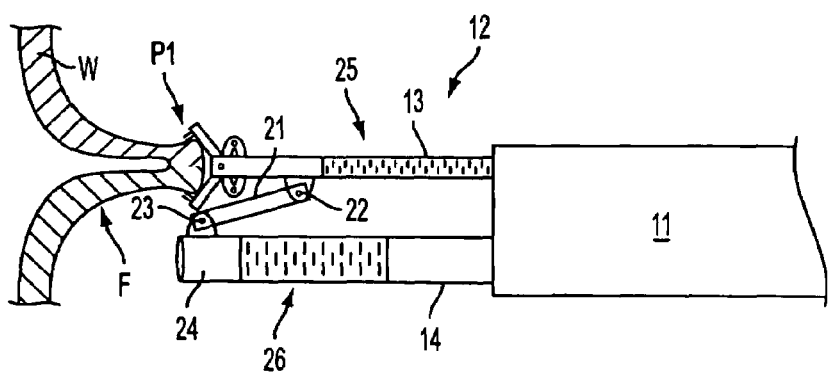

Referring to FIG. 3C, after the tissue wall has been engaged at contact point P1, flexible tube 13 is urged proximally within catheter 11 by further proximal retraction of control wire 19 to stretch tissue wall W and create tissue fold F. During this movement of flexible tube 13, link 21 of hinge assembly 20 causes tissue grabbing assembly 18 to move from a position distal to distal end 24 of flexible tube 14, to a position proximal of distal end 24 of flexible tube 14. Bendable sections 25 and 26 of flexible tubes 13 and 14, respectively, accommodate any lateral motion caused by operation of hinge assembly 20. Advantageously, formation of fold F facilitates the penetration of the tissue wall by a needle and subsequent delivery of an anchor assembly, as described hereinafter.

Figure 3D:
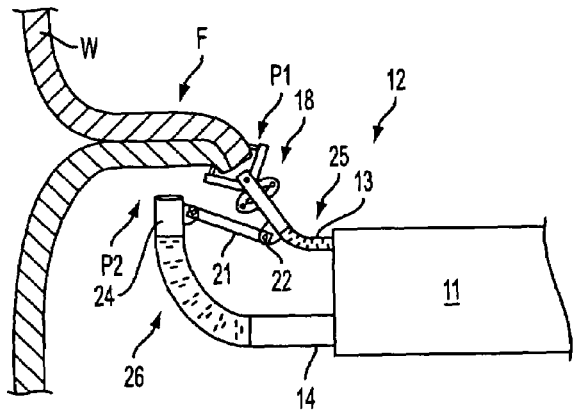
Figure 3E:
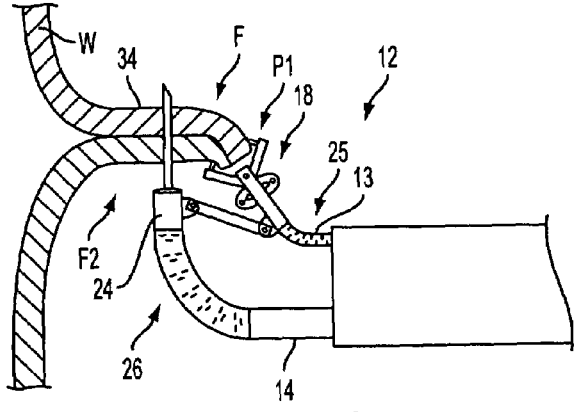

Referring to FIG. 3D, additional proximal movement of actuator 17 causes flexible tubes 13 and 14 to buckle at bendable sections 25 and 26. Hinge assembly 20 transmits force applied to flexible tube 13 via control wire 19 and actuator 17 to the distal tip 24. Preferably, flexible tube 14 is configured so that distal tip 24 contacts, and is substantially perpendicular, to tissue fold F at contact point P2. As illustrated in FIG. 3E, once tissue fold F is stretched across distal tip 24 of flexible tube 14, sharpened needle or obturator 34 may be extended from distal tip 24 of flexible tube 14 to pierce all four layers of the tissue wall W. Sharpened needle or obturator 34 is inserted via inlet 35 to flexible tube 14 on handle 16 (see FIG. 1A).

As discussed above, the GI lumen comprises an inner mucosal layer, connective tissue, the muscularis layer and the serosa layer. To obtain a durable purchase, e.g., in performing a stomach reduction procedure, the staples or anchors used to achieve reduction of the GI lumen must engage at least the muscularis tissue layer, and more preferably, the serosa layer as well. Advantageously, stretching of tissue fold F across distal tip 24 permits an anchor to be ejected through both the muscularis and serosa layers, thus enabling durable gastrointestinal tissue approximation.

As depicted in FIG. 3E, after tissue fold F is stretched across distal tip 24 of flexible tube 14 to form contact point P2 with tissue wall W, needle 34 may be extended from distal tip 24 and through tissue fold F. Because needle 34 penetrates the tissue wall twice, it exits within the gastrointestinal lumen, thus reducing the potential for injury to surrounding organs. Once the needle has penetrated tissue fold F, an anchor assembly is ejected through distal tip 24 as described hereinbelow.

Figure 4A:
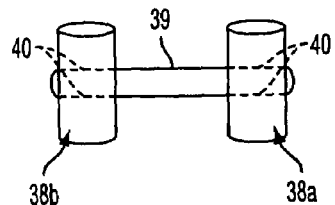
FIGS. 4A-4C are side-sectional views of an anchor assembly and delivery system suitable for use with apparatus of the present invention.
Figure 4B:
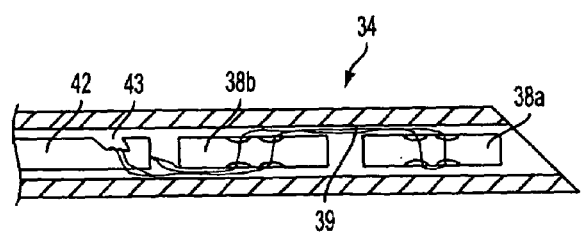
Figure 4C:
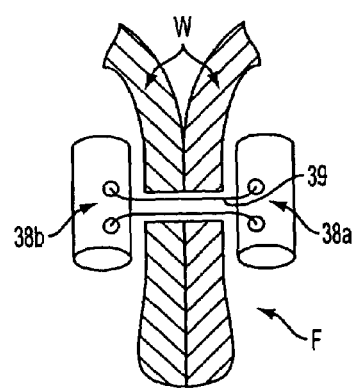

With respect to FIGS. 4A-4C, a first embodiment of an anchor assembly suitable for use with the apparatus of the present invention is described. Anchor assembly 36 comprises T-anchor assembly having distal rod 38a and proximal rod 38b connected by suture 39. The precise shape, size and materials of the anchors may vary for individual applications. In addition, the suture material also may vary for individual applications. By way of example, the suture material may consist of monofilament wire, multifilament wire or any other conventional suture material. Alternatively, suture 39 may comprise elastic material, e.g. a rubber band, to facilitate adjustment of the distance between the proximal and distal rods. Suture 39 extends through a pair of through-holes 40 in each rod, thereby forming a loop. Alternatively, suture 39 may be attached to the rods via an eyelet or using a suitable adhesive. Preferably, through-holes 40 are located near the center of the rods 38a and 38b.

Referring to FIG. 4B, rods 38a and 38b may be delivered through needle 34 (see FIG. 3E) using push rod 42. Push rod 42 is adapted to freely translate through flexible tube 14 and needle 34. Push rod 42 is preferably flexible, so that it may slide through bendable section 26 of flexible tube 14. In addition, push rod 42 may include notch 43 near its distal end to facilitate grasping and tensioning suture 39 after anchor delivery.

During anchor delivery, the longitudinal axis of distal rod 38a is substantially parallel to the longitudinal axis of needle 34. However, once distal rod 38a is ejected from needle 34, suture tension induces the rod to rotate approximately 90 degrees about its longitudinal axis, so that its longitudinal axis is substantially perpendicular to the longitudinal axis of needle 35. This rotation of distal rod 38a prevents it from being pulled back through tissue wall W.

Referring to FIG. 4C, once rod 38a is ejected on the distal side of fold F, needle 35 is retracted and push rod 42 is used to eject rod 38b on the proximal side of tissue fold F. Like distal rod 38a, tension in the suture causes proximal rod 38b to rotate about 90 degrees once it is ejected from the needle. Notch 43 in push rod 42 then may be employed to tighten suture 39 by any of a variety of mechanisms. Alternatively, suture 39 may comprise an elastic material that dynamically tightens the rods against tissue fold F.

Figure 5A:
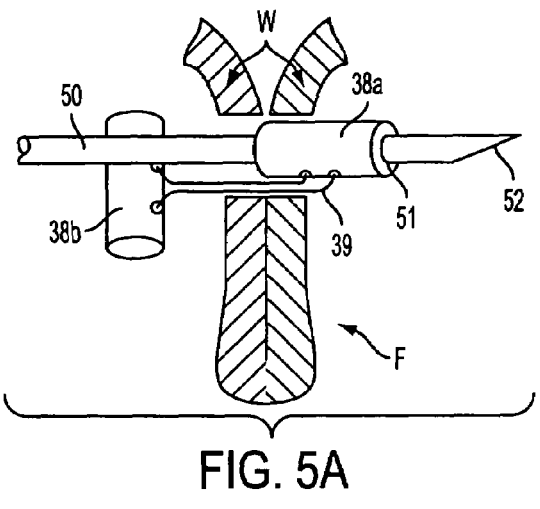
FIGS. 5A and 5B are side-sectional views of another anchor assembly suitable for use with apparatus of the present invention.

Referring now to FIG. 5A, according to other embodiments, the anchor assembly comprises a T-anchor assembly suitable to be disposed over obturator 50. More particularly, distal rod 38a includes through-hole 51 dimensioned for the passage of obturator tip 52, and obturator 50 is translatably inserted through flexible tube 14 via inlet 35 of handle 16 (see FIG. 1A). Proximal rod 38b may be a solid rod that does not include a through-hole for passage of obturator 50. Alternatively, proximal rod 38b may include a through-hole for the passage of the obturator. Preferably, obturator tip 52 is sharpened to facilitate tissue penetration.

Figure 5B:
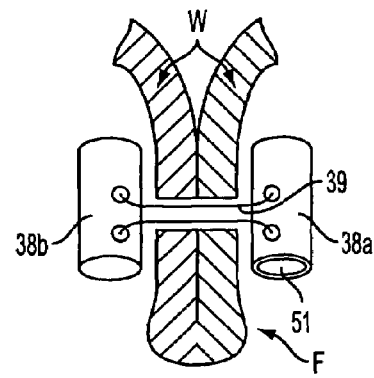

With respect to FIG. 5B, once rod 38a is ejected on the distal side of fold F, it rotates into a position substantially parallel to tissue wall W and perpendicular to the longitudinal axis of the obturator. Obturator 50 then is retracted and proximal rod 38b is ejected from flexible tube 14. More particularly, when flexible tube 14 is retracted from tissue wall W, proximal rod 38b is pulled through distal tip 24. Proximal rod 38b then rotates substantially 90 degrees as it is ejected from flexible tube 14 so that rod 38b is urged against tissue wall W.

Figure 6A:
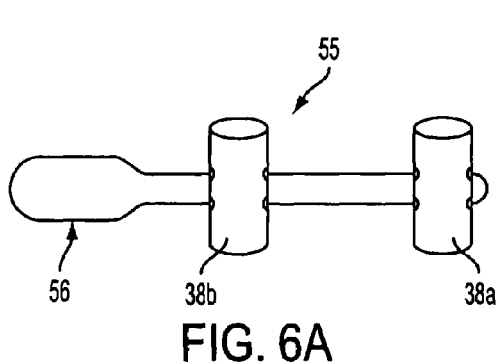
FIGS. 6A and 6B are side-sectional views of another alternative anchor assembly suitable for use with apparatus of the present invention.

Referring to FIG. 6A, according to further embodiments, anchor assembly 55 comprises a T-anchor assembly similar to the embodiment depicted in FIG. 4A. However, anchor assembly 55 includes fine wire tether 56 that may be twisted to maintain the tension between rods 38a and 38b.

Figure 6B:
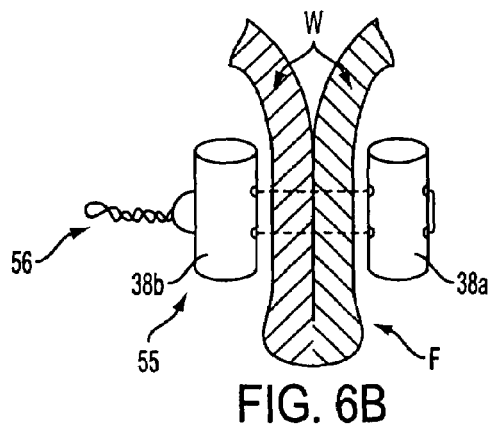

With respect to FIG. 6B, a method of delivering anchor assembly 55 is described. Initially, distal rod 38a is delivered across both tissue walls using needle 34. The needle then is retracted to release distal rod 38a so that it engages the tissue wall. Next, needle 34 is retracted to release proximal rod 38b, so that it too rotates into engagement with the tissue wall. A proximal portion of the wire tether is captured by notch 43 of push rod 42 (see FIG. 4B), and the push rod is rotated to cause proximal rod 38b to clamp down on the tissue fold. Because wire tether 56 is twisted by rotation of push rod 42, it maintains the desired force on the tissue walls.

Referring now to FIG. 7, a unidirectionally adjustable anchor assembly suitable for use with apparatus of the present invention is described. Anchor assembly 60 comprises distal anchor 62 and unidirectionally adjustable proximal anchor 64, which are connected by suture 39. Distal anchor 62 is translationally fixed with respect to suture 39. Such fixation may be achieved in a variety of ways. For example, as seen in FIG. 7A, distal anchor 62 may comprise a pair of through-holes 63, located near the center of anchor 62 and through which suture 39 is threaded and tied off at knot 65.

FIG. 7B provides alternative techniques for fixing the distal anchor. As seen in FIG. 7B(i), distal anchor 62 may comprise hollow tube T having opening O. A distal end of suture 39 is passed through opening O and formed into knot K, which is dimensioned such that it cannot pass through opening O, thereby fixing the distal anchor with respect to the suture. In order to facilitate formation of knot K, distal anchor 62 optionally may comprise distal opening DO, which is dimensioned such that knot K may pass therethrough. The distal end of suture 39 may be passed through distal opening DO, knotted, and then pulled back within hollow tube T of anchor 62 until it catches at opening O.

A drawback of the fixation technique described with respect to FIG. 7B(i) is a risk of suture 39 being torn or cut due to rubbing against opening O. In FIG. 7B(ii), hollow tube T comprises first end E to which is connected wire loop L, which may be formed, for example from a nickel-titanium alloy ("Nitinol"). Suture 39 passes through the wire loop before terminating at knot K. Knot K is dimensioned such that it cannot pass back through the wire loop. Wire loop L directs suture 39 through opening O, thereby reducing rubbing of the suture against the opening and reducing a risk of tearing or cutting of suture 39.

FIG. 7B(iii) provides yet another alternative technique for fixing the distal anchor with respect to the suture. Distal anchor 62 again comprises hollow tube T having opening O. Rod R is disposed within tube T, and the ends of the tube may be either closed or crimped to rod R, such that the rod is maintained within the tube. The distal end of suture 39 is threaded through opening O, around rod R, and back out opening O. The suture is then knotted at knot K, thereby fixing distal anchor 62 with respect to suture 39.

In addition to the techniques shown in FIGS. 7A and 7B, suture 39 alternatively may be fixed with respect to anchor 62 by other means, for example, via a knotted eyelet or via a suitable adhesive. Additional techniques will be apparent to those of skill in the art. While anchor 62 is illustratively shown as a rod- or T-type anchor, any of a variety of anchors, per se known, may be used as distal anchor 62. Exemplary anchors are described in co-pending U.S. patent application Ser. No. 10/612,170, filed Jul. 1, 2003, which is incorporated herein by reference in its entirety. Additional anchors are described hereinbelow with respect to FIG. 17.

Referring again to FIG. 7A, adjustable proximal anchor 64 comprises outer cylinder 66 having first end 67a and second end 67b, as well as first opening 68a and second opening 68b.

First and second openings 68 are preferably disposed near the center of cylinder 66 and approximately 180° apart. Anchor 64 further comprises first flexible rod 70a and second flexible rod 70b, both of which are disposed within outer cylinder 66 and coupled to first and second ends 67 of cylinder 66. Rods 70 may be formed, for example, from Nitinol or from a polymer, and may be separated from one another by small gap G. As with the previous anchor assemblies, the precise shape, size and materials of the anchors and suture may vary as required for specific applications.

As best seen in FIG. 7C, suture 39 passes from distal anchor 62 through first opening 68a of proximal anchor 64, around second flexible rod 70b, around first flexible rod 70a, between rods 70a and 70b, and out through second opening 68b. This suture winding provides a unidirectional adjustment capability that allows a length L of suture 39 disposed between distal anchor 62 and proximal anchor 64 to be shortened. However, the suture winding precludes an increase in length L. FIG. 8 illustrate the mechanism of this unidirectional adjustment capability in greater detail. Optionally, suture 39 may be tied off proximal of anchor 64 at knot 69, thereby forming a proximal loop of suture to facilitate deployment and/or adjustment of anchor assembly 60.

Figure 8A:
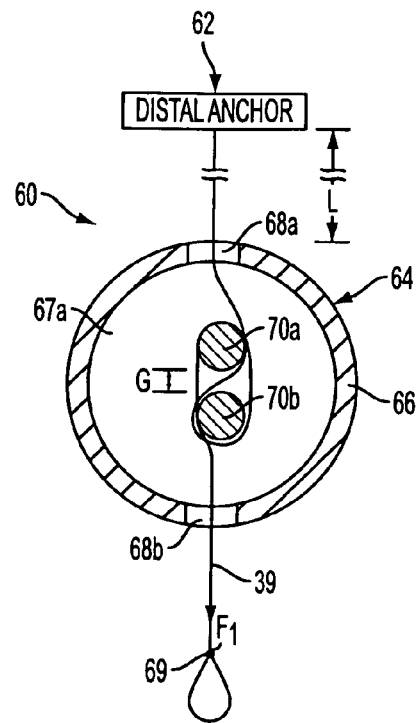
FIGS. 8A and 8B are schematic cross-sectional views illustrating the unidirectional adjustment capability of the anchor assembly of FIG. 7.

In FIG. 8A, a proximally-directed force $F_1$ is applied to suture 39 proximal of adjustable anchor 64, while anchor 64 is held stationary or is advanced distally. A portion of force $F_1$ is transferred through suture 39 to second flexible rod 70b, which causes rod 70b to bow, thereby increasing gap G and allowing suture 39 to freely pass between rods 70a and 70b and through proximal anchor 64, facilitating unidirectional adjustment. When anchor 64 is held stationary while suture 39 is retracted proximally, distal anchor 62 retracts proximally towards anchor 64. Alternatively, when anchor 64 is advanced distally while suture 39 is retracted proximally, distal anchor 62 either remains stationary or retracts proximally towards proximal anchor 64, depending upon a degree of distal advancement of proximal anchor 64. Regardless, length L of suture 39 disposed between anchors 62 and 64 is decreased, thereby unidirectionally adjusting a distance between the anchors.

Figure 8B:
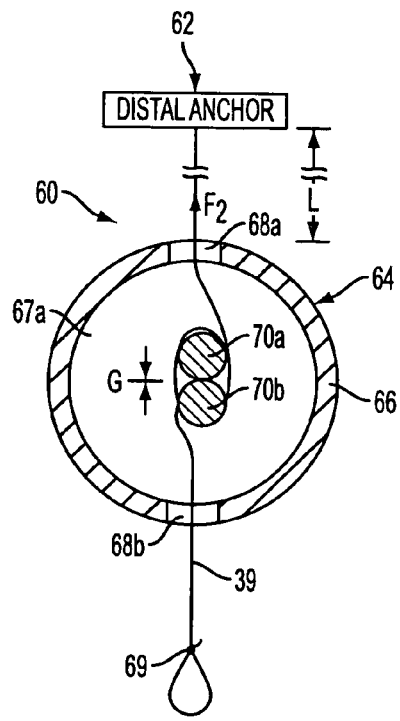

In FIG. 8B, a distally-directed force $F_2$ is applied to suture 39 distal of adjustable anchor 64. Force $F_2$ may be applied, for example, by tissue compressed between anchors 62 and 64. Compressed tissue stores energy in a manner similar to a compression spring and seeks to push anchors 62 and 64 apart after unidirectional tightening. Force $F_2$ causes the loop of suture 39 around first and second rods 70 to tighten, thereby bowing both rods inward and closing gap G such that suture 39 is friction locked between first and second flexible rods 70. In this manner, the length L of suture between anchors 62 and 64 may be selectively decreased but cannot be increased.

As will be apparent to those of skill in the art, the magnitude of force required to unidirectionally adjust length L may be altered in a variety of ways. For example, a length, flexibility or diameter of rods 70 may be altered. Likewise, the elasticity or diameter of suture 39 may be altered. Initial gap G may be increased or decreased. Furtherstill, the materials used to form rods 70 and suture 39 may be changed to alter material properties, such as coefficients of friction, and/or rods 70 or suture 39 may comprise a lubricious coating. Additional methods for varying the magnitude of force, a few of which are described hereinbelow with respect to FIG. 9, will be apparent in view of this disclosure and are included in the present invention.

Figure 9A:
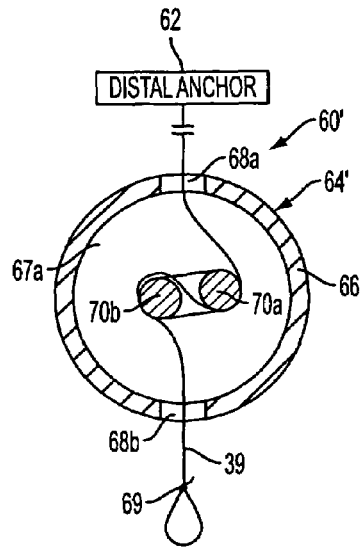
FIGS. 9A-9C are schematic cross-sectional views of alternative embodiments of the proximal anchor of the anchor assembly of FIG. 7.
Figure 9B:
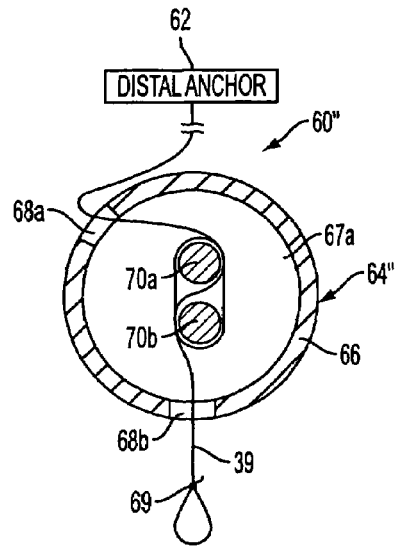

Referring now to FIG. 9, alternative anchors 64 are described. In FIG. 9A, flexible rods 70 of proximal adjustable anchor 64' are rotated with respect to openings 68 (or vice versa). When utilizing the suture winding described in FIGS. 7 and 8, rotation of rods 70 up to 180° clockwise progressively increases friction when force is applied to anchors 62 and 64. The magnitude of the friction lock is increased when force is applied in the manner described with respect to FIG. 8B. However, friction is also increased when unidirectionally adjusting the length of suture between the proximal and distal anchors by applying force in the manner described with respect to FIG. 8A. Rotation of rods 70 more than about 180° clockwise would cause anchor 64' to friction lock regardless of which direction force were applied to suture 39, thereby negating the unidirectional adjustment capability. Counterclockwise rotation of rods 70 with respect to openings 68 would initially reduce friction during force application to suture 39 in either direction. It is expected that counterclockwise rotation in excess of about 90° would eliminate the friction lock described in FIG. 8B and allow bidirectional adjustment. Continued counterclockwise rotation beyond about 450° would reverse the directions of friction lock and unidirectional adjustment, while counterclockwise rotation beyond about 720° would result in friction lock regardless of which direction force were applied to suture 39.

As discussed previously, openings 68 of cylinder 66 of anchor 64 are preferably disposed approximately 180° apart from one another. However, in order to increase the friction lock force without significantly increasing friction during unidirectional adjustment, first opening 68a may be rotated counterclockwise with respect to second opening 68b (or vice versa), as seen with anchor 64" of FIG. 9B. In this manner, first opening 68a is no longer in line with rods 70, while second opening 68b remains in line with rods 70. When force $F_1$ is applied to anchor 64", second flexible rod 70b is able to bow outward and increase gap G, thereby facilitating unidirectional adjustment. Likewise, when force $F_2$ is applied to the anchor, gap G is closed more tightly upon suture 39, thereby increasing the friction lock force. If first opening 68a alternatively were rotated clockwise with respect to the second opening, it is expected that the friction lock force would be decreased.

Figure 9C:
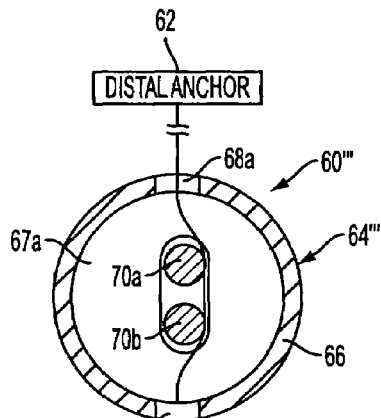

In FIG. 9C, proximal adjustable anchor 64''' comprises an alternative suture winding. Suture 39 passes from distal anchor 62 through first opening 68a of anchor 64''', around second flexible rod 70b, around first flexible rod 70a, back around second flexible rod 70b, between rods 70a and 70b, and out through second opening 68b. As with the suture winding described with respect to anchor 64 of FIGS. 7 and 8, the suture winding illustrated in FIG. 9C provides a unidirectional adjustment capability that allows a length L of suture 39 disposed between distal anchor 62 and proximal anchor 64''' to be shortened. However, this suture winding precludes an increase in length L. Additional unidirectionally adjustable suture windings will be apparent to those of skill in the art.

With reference to FIG. 10, an alternative unidirectionally adjustable anchor comprising three rods is described. Anchor assembly 80 comprises distal anchor 62 and proximal anchor 82. Unidirectionally adjustable proximal anchor 82 comprises outer cylinder 84 having first end 85a and second end 85b (not shown), as well as first opening 86a and second opening 86b. First and second openings 86 are preferably disposed near the center of cylinder 84 and approximately 180° apart. Anchor 82 further comprises first flexible rod 88a, second flexible rod 88b and third flexible rod 88c, all of which are disposed within outer cylinder 66 and coupled to first and second ends 85 of cylinder 64. Rods 88 are separated from one another by gaps $G_1$ and $G_2$.

Figure 10A:
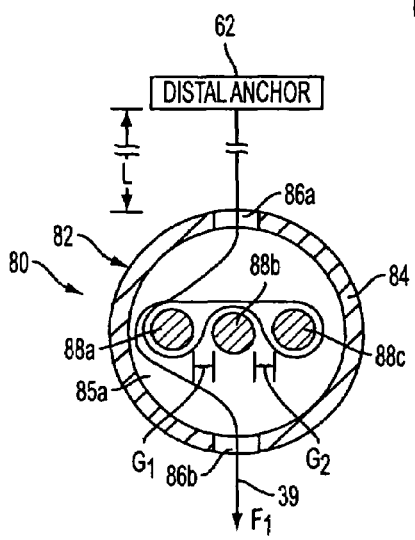
FIGS. 10A and 10B are schematic cross-sectional views of an alternative unidirectionally adjustable anchor assembly suitable for use with apparatus of the present invention.
Figure 10B:
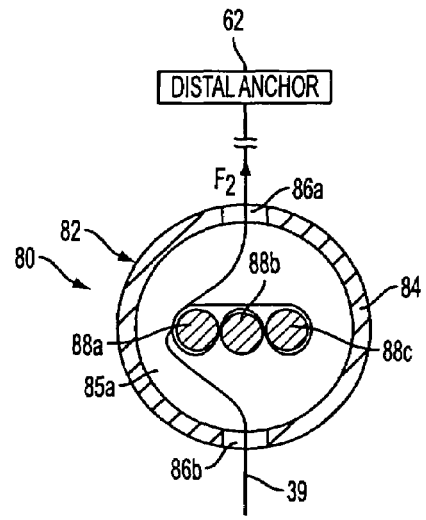

Suture 39 passes from distal anchor 62 through first opening 86a of proximal anchor 82, around first rod 88a, between first rod 88a and second rod 88b, between second rod 88b and third rod 88c, around third rod 88c, back to and around first rod 88a, and out through second opening 86b. As seen in FIG. 10A, when force $F_1$ is applied to suture 39, gaps $G_1$ and $G_2$ remain open, thereby facilitating unidirectional adjustment/shortening of length L of suture 39 disposed between distal anchor 62 and proximal anchor 82. As seen in FIG. 10B, when force $F_2$ is applied to suture 39, gaps $G_1$ and $G_2$ close down upon suture 39, thereby forming a friction lock that precludes an increase in length L of suture 39.

Referring now to FIG. 11, an alternative three rod anchor assembly is described. The unidirectionally adjustable anchors described hereinabove with respect to FIGS. 7-10 all comprise rods disposed within a cylinder having openings for passage of a suture. The openings act to center the suture with respect to the rods and can be used to alter magnitudes of force applied during adjustment and friction locking, as discussed previously. However, such openings present a risk of tearing or cutting the suture as the suture slides through the openings.

As seen in FIG. 11, anchor assembly 90 comprises distal anchor 62 and proximal anchor 92. Unidirectionally adjustable proximal anchor 92 comprises first flexible rod 94a and second flexible rod 94b, as well as rigid rod 96, which is preferably larger in diameter than first and second rods 94. Flexible rods 94 are preferably fabricated from Nitinol or a polymer, while rigid rod 96 is preferably fabricated from stainless steel or a polymer. Alternative materials will be apparent to those of skill in the art.

Anchor 92 further comprises first outer cylinder 98a and second outer cylinder 98b, which are crimped to the ends of first and second rods 94, and rigid rod 96. As an alternative to crimping, first and second cylinders 98 may each comprise an end cap (not shown) to which the rods are coupled. First and second cylinders 94 do not span a central portion of anchor 92. Flexible rods 94 are separated from one another by gap $G_1$, while rods 94 are separated from rigid rod 96 by gap $G_2$.

Figure 11A:
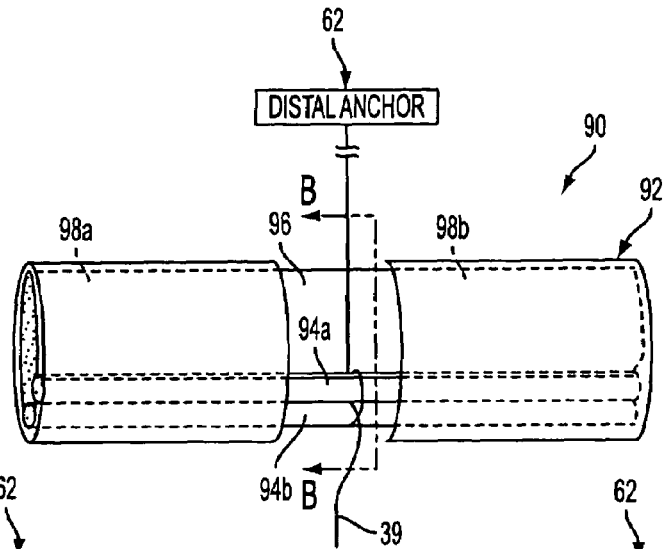
FIGS. 11A-11C are, respectively, a schematic side-view of another alternative unidirectionally adjustable anchor assembly suitable for use with the present invention, and cross-sectional views of the same taken along section line B-B of FIG. 11A.
Figure 11B:
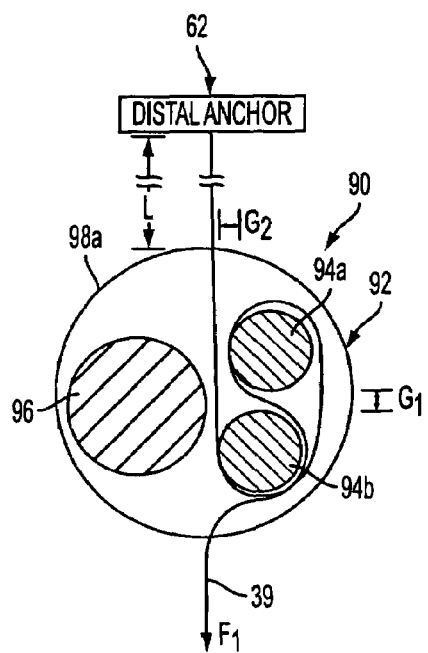
Figure 11C:
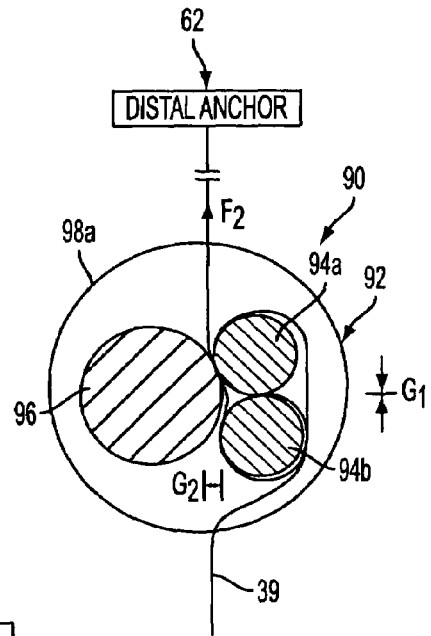

Anchor 92 comprises three rods, but, unlike anchor 82 of FIG. 10, suture 39 is only wrapped around two of them to achieve unidirectional adjustment. As best seen in FIGS. 11B and 11C, the illustrative suture winding of anchor assembly 90 is similar to that described previously with respect to anchor assembly 60 of FIGS. 7 and 8. The break between first and second cylinders 98 acts to center suture 39 with respect to the rods, as seen in FIG. 11A, while rigid rod 96 acts to stiffen and reduce rotation of anchor 92 as it directs suture 39 about flexible rods 94.

Suture 39 passes from distal anchor 62 to proximal anchor 92, between rigid rod 96 and flexible rods 94, around second flexible rod 94b, around first flexible rod 94a, between rigid rod 96 and first flexible rod 94a, between flexible rods 94a and 94b, and out. As seen in FIG. 11A, when force $F_1$ is applied to suture 39, flexible rods 94 are forced apart and gap $G_1$ widens while gap $G_2$ remains substantially constant, thereby allowing unidirectional adjustment of length L of suture 39 disposed between distal anchor 62 and proximal anchor 92. As seen in FIG. 11B, when force $F_2$ is applied to suture 39, gap $G_1$ closes down upon suture 39, thereby forming a friction lock that precludes an increase in length L of suture 39. Gap $G_2$ again remains substantially constant.

Figure 12:
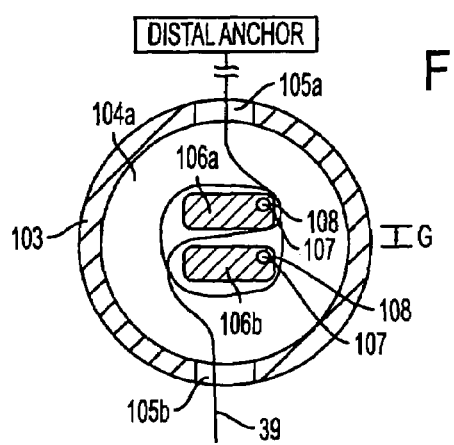
FIG. 12 is a schematic cross-sectional view of an alternative unidirectionally adjustable anchor assembly comprising pivoting paddles.

With reference to FIG. 12, an alternative unidirectionally adjustable anchor assembly comprising pivots is described. Anchor assembly 100 comprises distal anchor 62 and proximal anchor 102. Unidirectionally adjustable proximal anchor 102 comprises outer cylinder 103 having first end 104a and second end 104b (not shown), as well as first opening 105a and second opening 105b. First and second openings 105 are preferably disposed near the center of cylinder 103 and approximately 180° apart. Anchor 102 further comprises first rod or paddle 106a and second rod or paddle 106b, both of which are disposed within outer cylinder 103 and coupled to the first and second ends of cylinder 103 by pins 107, which pass through pivot holes 108. In this manner, first and second paddles 106 are able to rotate about pivot holes 108. Paddles 106 may be formed, for example, from stainless steel or a polymer, and are separated from one another by gap G. As with the previous anchor assemblies, the precise shape, size and materials of the anchors, as well as suture 39, may vary as required for specific applications.

Suture 39 illustratively passes from distal anchor 62 through first opening 105a of proximal anchor 102, around second paddle 106b, around first paddle 106a, between paddles 106a and 106b, and out through second opening 105b. The placement of pivot holes 108 ensures that application of force $F_1$, as described hereinabove, causes paddles 106 to rotate apart from one another and expand gap G, thereby enabling unidirectional adjustment. Likewise, application of previously discussed force $F_2$ causes paddles 106 to rotate together, thereby closing gap G and pinching suture 39 between the paddles in a friction lock. An increase in the magnitude of force $F_2$ serves to rotate paddles 106 together more tightly, thereby increasing the magnitude of the friction lock acting upon suture 39 between the paddles. In this manner, unidirectional adjustment is achieved.

Figure 13:
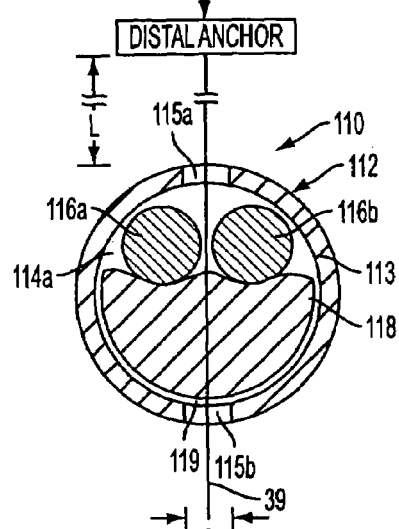
FIG. 13 is a schematic cross-sectional view of an alternative unidirectionally adjustable anchor assembly comprising spring material.

Referring now to FIG. 13, an alternative unidirectionally adjustable anchor assembly comprising spring material is described. Anchor assembly 110 comprises distal anchor 62 and proximal anchor 112. Unidirectionally adjustable proximal anchor 112 comprises outer cylinder 113 having first end 114a and second end 114b (not shown), as well as first opening 115a and second opening 115b. First and second openings 115 are preferably disposed near the center of cylinder 113 and approximately 180° apart. Anchor 112 further comprises first rod 116a and second rod 116b that are separated by gap G, as well as spring material 118, all of which are disposed within outer cylinder 113. Spring material 118 abuts rods 116, which preferably are substantially the same length as cylinder 113, and may either move freely within cylinder 113 or may be coupled to the ends (not shown) of cylinder 113. Spring material 118 may also move freely within cylinder 113 or may be coupled to the cylinder, and comprises lumen 119 having a diameter that is preferably equal to or less than the diameter of suture 39. Spring material 118 may comprise, for example, a compressible biocompatible foam, which acts as a compression spring.

Suture 39 passes from distal anchor 62 to proximal anchor 112 through first opening 115a of cylinder 113, between rods 116, through lumen 119 of spring material 118, and out through second opening 115b. Lumen 119 snugly contacts suture 39 such that application of force $F_1$ causes friction between the suture and the spring material to compress the spring material against the wall of cylinder 114, thereby reducing a stress applied to rods 116 by spring material 118 and increasing gap G such that unidirectional adjustment of length L of suture 39 disposed between distal anchor 62 and proximal anchor 102 may proceed. Application of force $F_2$ stretches spring material 118 against rods 116, thereby increasing the stress applied to the rods by the spring material and closing gap G such that suture 39 is friction locked between rods 116.

Figure 14A:
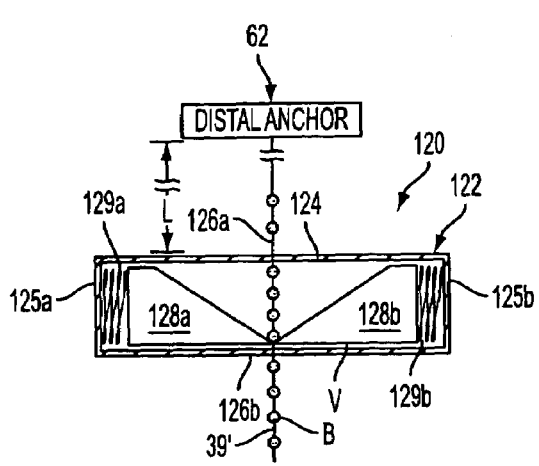
FIGS. 14A-14B are schematic side-sectional views of alternative unidirectionally adjustable anchor assemblies comprising one-way valves.

With reference to FIG. 14, alternative unidirectionally adjustable anchor assemblies comprising one-way valves are described. In FIG. 14A, anchor assembly 120 comprises distal anchor 62 and proximal anchor 122. Unidirectionally adjustable proximal anchor 122 comprises outer cylinder 124 having first and second ends 125a and 125b, as well as first opening 126a and second opening 126b. First and second openings 126 are preferably disposed near the center of cylinder 124 and approximately 180° apart. Anchor 122 further comprises first inclined plane 128a and second inclined plane 128b, which are forced into apposition by compression springs 129a and 129b, thereby forming one-way valve V at the junction of the two inclined planes. Inclined planes 128 and springs 129 are disposed within outer cylinder 124; springs 129 abut ends 125 of cylinder 124, as well as the ends of the inclined planes. Suture 39' comprises a plurality of knots or beads B adapted to actuate one-way valve V.

Suture 39' passes from distal anchor 62 to proximal anchor 122 through first opening 126a of cylinder 124, between inclined planes 128, through one-way valve V, and out through second opening 126b. Application of force $F_1$ to suture 39' causes a bead B to contact inclined planes 128 and gradually coax them apart by compressing springs 129, thereby opening valve V and allowing the bead to pass through the valve. Once the bead has passed through valve V, springs 129 force inclined planes 128 back into apposition, thereby closing the valve. Continued application of force $F_1$ allows multiple beads to pass through the valve, which facilitates unidirectional adjustment of suture length L disposed between distal anchor 62 and proximal anchor 122. Application of force $F_2$ causes a bead B of suture 39' to impinge upon the proximal sides of inclined planes 128. However, force transferred to the planes by the bead is perpendicular to the direction required to compress springs 129 and urge planes 128 apart. As such, the bead B impinging upon the proximal sides of planes 128 is not able to open one-way valve V and pass back through the valve in a distal direction, thereby ensuring only unidirectional adjustment, i.e. shortening, of the length L of suture disposed between the proximal and distal anchors.

Figure 14B:
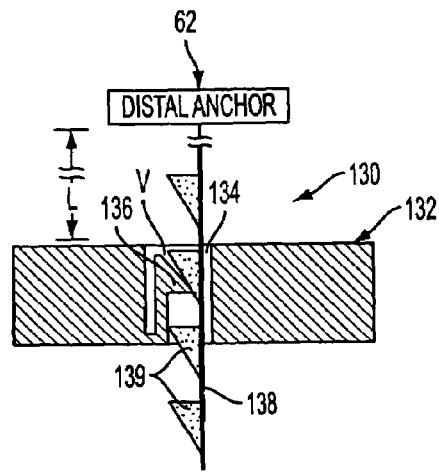

In FIG. 14B, an alternative unidirectionally adjustable anchor having a one-way valve is described. Anchor assembly 130 comprises distal anchor 62 and proximal anchor 132. Unidirectionally adjustable proximal anchor 132 comprises lumen 134 having cantilevered inclined plane 136 disposed therein, which forms one-way valve V. 'Zip-tie' fastener 138, having a plurality of inclined planes 139, connects proximal anchor 132 and distal anchor 62. The plurality of inclined planes 139 are disposed about 180° out of phase with inclined plane 136 of anchor 132.

Fastener 138 passes from distal anchor 62 to proximal anchor 132, through lumen 134 and past inclined plane 136. Inclined planes 139 of fastener 138 mesh with inclined plane 136 and bend or cantilever plane 136, such that planes 139 of fastener 138 may proximally pass one-way valve V when force $F_1$ is applied to the fastener, thereby enabling unidirectional adjustment of length L of fastener 138 disposed between the proximal and distal anchors. Conversely, when force $F_2$ is applied to the fastener, the proximal side of inclined plane 136 of anchor 132 abuts the distal side of an inclined plane 139 of fastener 138, and the fastener cannot be drawn distally through proximal anchor 132, nor can the length L of fastener disposed between the anchors be increased significantly.

Figure 15A:
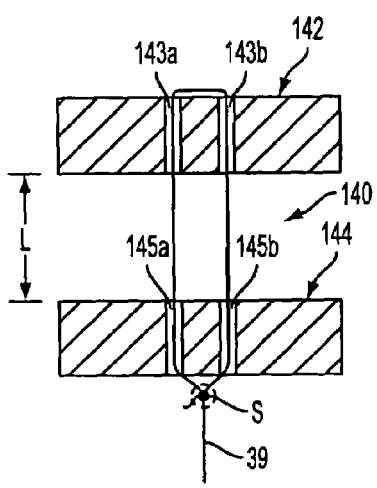
FIGS. 15A-15C are side-sectional and detail views of alternative unidirectionally adjustable anchor assemblies comprising slipknots.

Referring now to FIG. 15, alternative unidirectionally adjustable anchor assemblies comprising a slipknot are described. In FIG. 15A, anchor assembly 140 comprises distal anchor 142 and proximal anchor 144. Through-holes 143a and 143b extend through distal anchor 142, while through-holes 145a and 145b extend through proximal anchor 145. Preferably, through-holes 143 and 145 are located near the center of anchors 142 and 144, respectively.

Figure 15B:
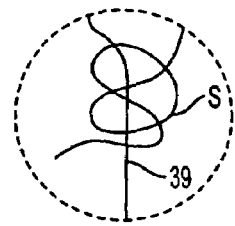

The distal end of suture 39 passes through through-hole 145a of proximal anchor 144 to distal anchor 142, where it passes through through-hole 143a and back through through-hole 143b. It then extends from distal anchor 142 back to proximal anchor 144, where it passes through through-hole 145b of the proximal anchor. The distal end of suture 39 is tied off at unidirectional slipknot S, which is located proximal of anchor 144. FIG. 15B provides a detail view illustrating formation of slipknot S.

As will be apparent to those of skill in the art, application of force $F_1$ causes suture 39 to slide through through-holes 143 and 145, and decrease the length L of suture 39 disposed between anchors 142 and 144. Suture 39 may readily pass through slipknot S in a proximal direction, thereby facilitating unidirectional adjustment of length L. However, application of force $F_2$ tightens slipknot S and prohibits passage of suture 39 through the slipknot in a distal direction, thereby precluding an increase in length L.

Figure 15C:
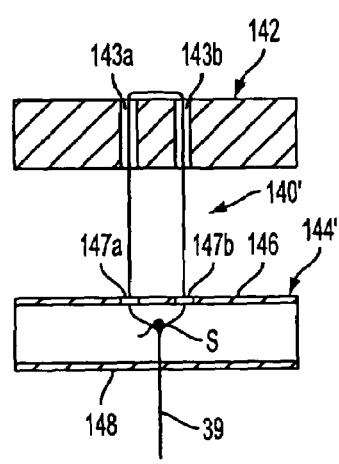

FIG. 15C illustrates an alternative embodiment of anchor assembly 140 wherein the slipknot is disposed within the proximal anchor. Anchor assembly 140' comprises distal anchor 142 and proximal anchor 144'. Proximal anchor 144' comprises hollow cylinder or tube 146 having distal openings 147a and 147b, and proximal opening 148.

The distal end of suture 39 passes through proximal opening 148 into the interior of tube 146. It then passes through distal opening 147a of proximal anchor 144' to distal anchor 142, where it passes through through-hole 143a and back through through-hole 143b. Next, suture 39 extends from distal anchor 142 back to proximal anchor 144', where it passes through distal opening 147b into the interior of tube 146 of the proximal anchor. The distal end of suture 39 is tied off at unidirectional slipknot S, which is disposed within tube 146 of anchor 144'. Anchor assembly 140' may be unidirectionally adjusted in a manner similar to that described hereinabove with respect to anchor assembly 140 of FIG. 15A.

FIGS. 7-15 illustrate anchor assemblies comprising various mechanisms for achieving unidirectional adjustment of the distance between the proximal and distal anchors. These mechanisms have been provided solely for the sake of illustration and should in no way be construed as limiting. Additional mechanisms for achieving unidirectional adjustment will be apparent to those of skill in the art in view of this disclosure and are included in the present invention. Furthermore, a majority of the anchor assemblies of FIGS. 7-15 have been described with the distal anchor being fixed relative to the suture, and the proximal anchor being adjustable. However, it should be understood that the distal anchor may alternatively be adjustable and the proximal anchor may be fixed, and/or both anchors may be unidirectionally adjustable, as with anchor assembly 140 of FIG. 15.

Figure 16A:
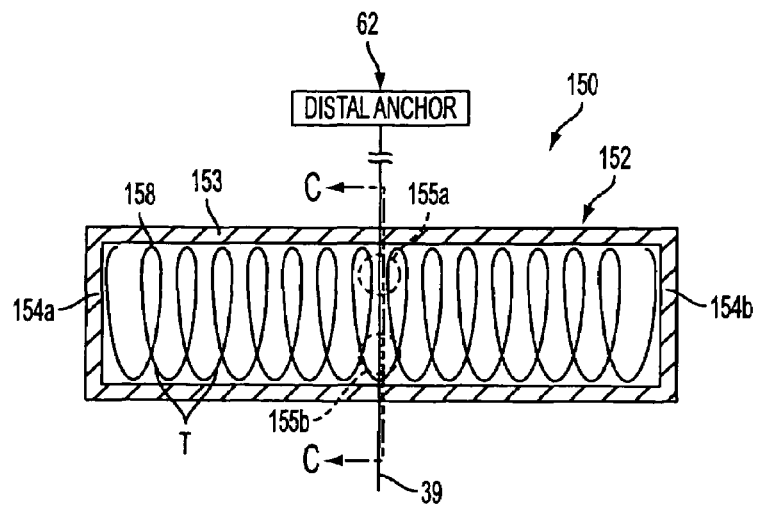
FIGS. 16A-16C are, respectively, a schematic side-sectional view of a bi-directionally adjustable anchor assembly comprising a locking mechanism, and cross-sectional views of the same taken along section line C-C of FIG. 16A.

With reference now to FIG. 16, a bi-directionally adjustable anchor assembly comprising a locking mechanism is described. Anchor assembly 150 comprises distal anchor 62 and proximal anchor 152. As seen in FIG. 16A, bi-directionally adjustable proximal anchor 152 comprises outer cylinder 153 having first end 154a and second end 154b, as well as first opening 155a and second opening 155b. First and second openings 155 are preferably disposed near the center of cylinder 153 and approximately 90° apart. Proximal anchor 152 further comprises tension spring 158 disposed within outer cylinder 153.

Figure 16B:
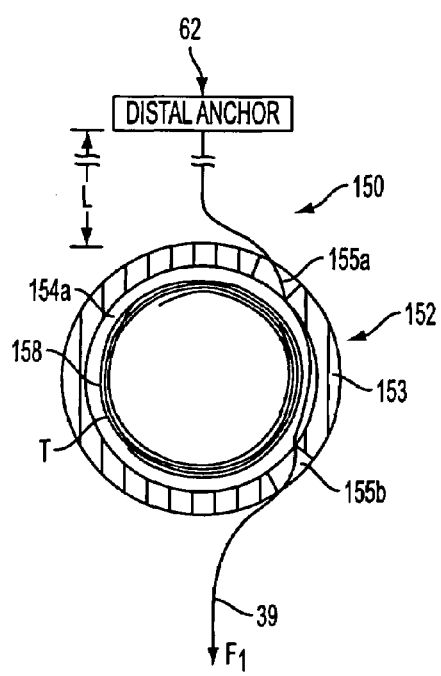
Figure 16C:
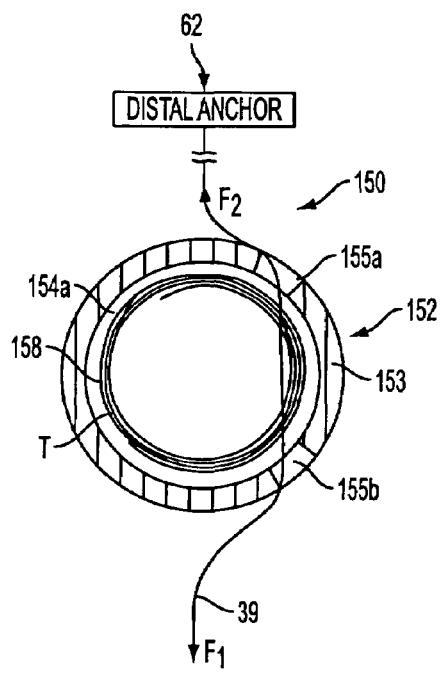

As seen in FIG. 16B, suture 39 passes from distal anchor 62 to proximal anchor 152 through first opening 155a, around spring 158, and out through second opening 155b. Suture 39 moves freely about tension spring 158 in either direction during application of force $F_1$ or force $F_2$, thereby facilitating bi-directional adjustment of suture length L disposed between the proximal and distal anchors. However, as seen in FIG. 16C, simultaneous application of forces $F_1$ and $F_2$ with sufficient magnitude causes suture 39 to force threads T of spring 158 apart, such that suture 39 is trapped between threads T and locked in position, thereby precluding further adjustment of suture length L.

The magnitude of forces required to actuate the locking mechanism of proximal anchor 152 and lock suture 39 within threads T of spring 158 may be specified/altered in a variety of ways. For example, the angular spacing of openings 155 about outer cylinder 153 may be altered, the spring constant of spring 158 may be specified, and/or spring 158 or suture 39 may comprise a lubricious coating. Additional techniques will be apparent to those of skill in the art. It is expected that simultaneous application of forces $F_1$ and $F_2$ will be encountered when anchor assembly 150 has been deployed across a tissue fold and suture length L has been adjusted such that the tissue fold is compressed. A medical practitioner would then apply force $F_1$, while the compressed tissue fold would apply force $F_2$.

Although the anchor assemblies of FIGS. 10-16 have illustratively been described without knots or loops of suture or fastener disposed proximal of the proximal anchor (as seen, for example, with knot 69 on suture 39 of anchor assembly 60 in FIGS. 7 and 8) it should be understood that such loops or knots optionally may be provided in order to facilitate deployment and/or adjustment of the anchor assemblies. Additionally, the previously described anchor assemblies illustratively comprise distal rod- or T-type anchors. However, it should be understood that distal T-anchors have only been provided for the sake of illustration. The distal anchors (as well as the proximal anchors) may comprise any of a variety of anchors, per se known. Exemplary anchors are described in co-pending U.S. patent application Ser. No. 10/612,170, filed Jul. 1, 2003, which is incorporated herein by reference in its entirety. Additional anchors are described hereinbelow with respect to FIG. 17.

Figure 17A:
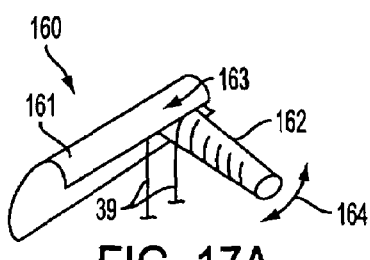
FIGS. 17A-17D are perspective views of alternative anchors suitable for use with the anchor assemblies of the present invention.

Referring to FIG. 17A, articulating anchor 160 includes semi-cylindrical base 161, rod 162 and suture 39. Rod 162 rotates about pivot point 163 (as indicated by arrow 164) between an expanded position (shown in FIG. 7A) and a reduced profile position, wherein rod 162 pivots within the semi-cylindrical base 161. Articulating anchor 160 may be delivered through a tissue fold using needle 34 described hereinabove with respect to FIG. 3E. Preferably, articulating anchor 160 is biased in the expanded position so that it automatically expands once it is ejected from the needle.

Figure 17B:
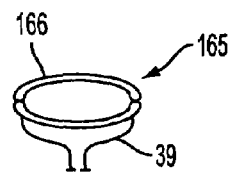
Figure 17C:
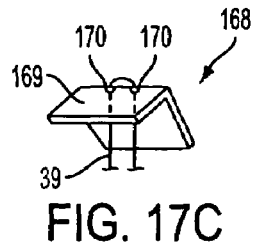
Figure 17D:
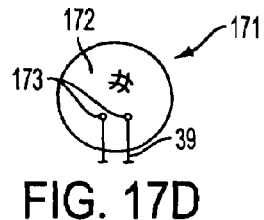

With respect to FIGS. 17B and 17C the anchors of the present invention also may comprise one or more oblong bodies connected by at least one suture. In FIG. 17B, anchor 165 comprises elliptical ring 166 having sutures 39 attached at substantially opposite sides of the ring. In FIG. 17C, anchor 168 comprises angle bracket 169 having a pair of through-holes 170 for suture 39. In FIG. 17D, anchor 171 comprises oblong bead 172 having a pair of through-holes 173 for suture 39. All three anchors 165, 168 and 171 (as well as the T-anchors described previously) have a first dimension (e.g., width) that is substantially larger than a second dimension (e.g., height). This dimensional difference necessitates that anchors 165, 168 and 171 be inserted within needle (e.g., needle 34 of FIG. 3E) in a particular orientation. Once the anchor is ejected through a tissue wall, tension on suture 39 forces the anchor to rotate so that it cannot be pulled back through the tissue wall. As will be understood by those of skill in the art, numerous other anchors may be employed without departing from the scope of the present invention.

Figure 18A:
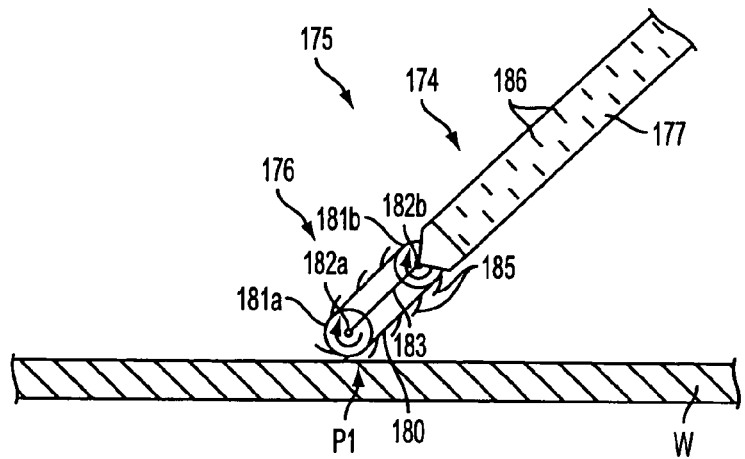
FIGS. 18A-18D are side views of alternative apparatus for forming a gastrointestinal fold.

Referring now to FIG. 18A, an alternative embodiment of apparatus for forming a tissue fold, constructed in accordance with the principles of the present invention, is described. Apparatus 175 comprises treadmill assembly 176 disposed at distal tip 174 of flexible tube 177. Flexible tube 177 is configured to be inserted through a patient's mouth, esophagus and into the stomach. Treadmill assembly 176 comprises conveyor 180 that circles around a pair of hubs 181a and 181b. Hubs 181a and 181b rotate about axles 182a and 182b, respectively, and are interconnected by bracket 183. A plurality of barbs or needles 185 is disposed at substantially regular intervals around the circumference of conveyor 180.

Flexible tube 177 preferably includes a plurality of through-wall slots 186 to enhance flexibility of the tube, yet maintain torqueability. Preferably, flexible tube 177 is made from stainless steel with an etched or laser-cut slot pattern. Preferably, the slot pattern is a sinusoidal repeating pattern of slots perpendicular to the longitudinal axis of the tube.

Figure 18B:
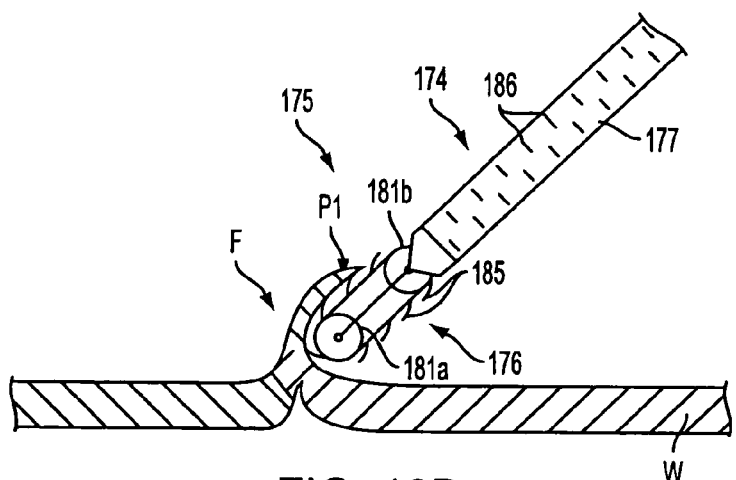
Figure 19:
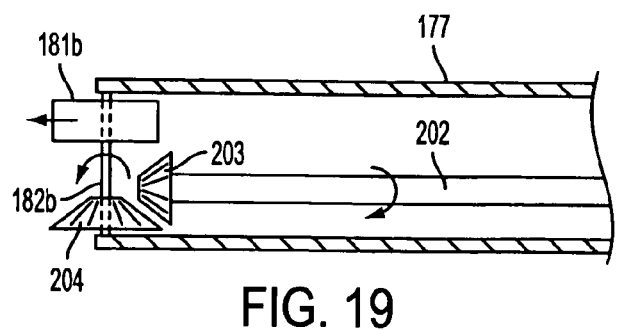
FIG. 19 is a cross-sectional view of the apparatus of FIGS. 18A-18D.

Referring to FIGS. 18 and 19, transmission of motive force to treadmill assembly 176 is described. In particular, drive shaft 202 disposed within flexible tube 177 is coupled to a manual knob or motor located at the proximal end of the catheter. The distal tip of drive shaft 202 is provided with beveled gear 203 that meshes with beveled gear 204 provided on axle 182b. Accordingly, rotation of beveled gear 203 is transmitted to beveled gear 204, thereby causing axle 182b to rotate. Axle 182b in turn rotates hub 181b, actuating conveyor 180. Reversing the rotation of drive shaft 202 reverses the direction of conveyor 180.

Referring again to FIGS. 18A-18D, a method of forming a gastrointestinal tissue fold F using apparatus 175 is described. In FIG. 18A, flexible tube 177 is positioned transesophageally so that treadmill assembly 176 contacts tissue wall W. Preferably, contact should be made at an angle relative to the tissue wall W. For example, an angle of approximately 45 degrees is depicted in FIG. 8A, while many other angles may be used without departing from the scope of the present invention.

When treadmill assembly 176 contacts tissue wall W, needle 185 engages the tissue at contact point P1 as the needle moves around distal hub 181a. As depicted in FIG. 18B, as the needle moves away from distal hub 181a, tissue wall W is pulled towards proximal end 181b, thereby forming a small tissue fold F. As the treadmill assembly continues to turn, subsequent needles 185 engage the tissue wall so that it becomes securely engaged to treadmill assembly 176 along the length of conveyor 180.

Figure 18C:
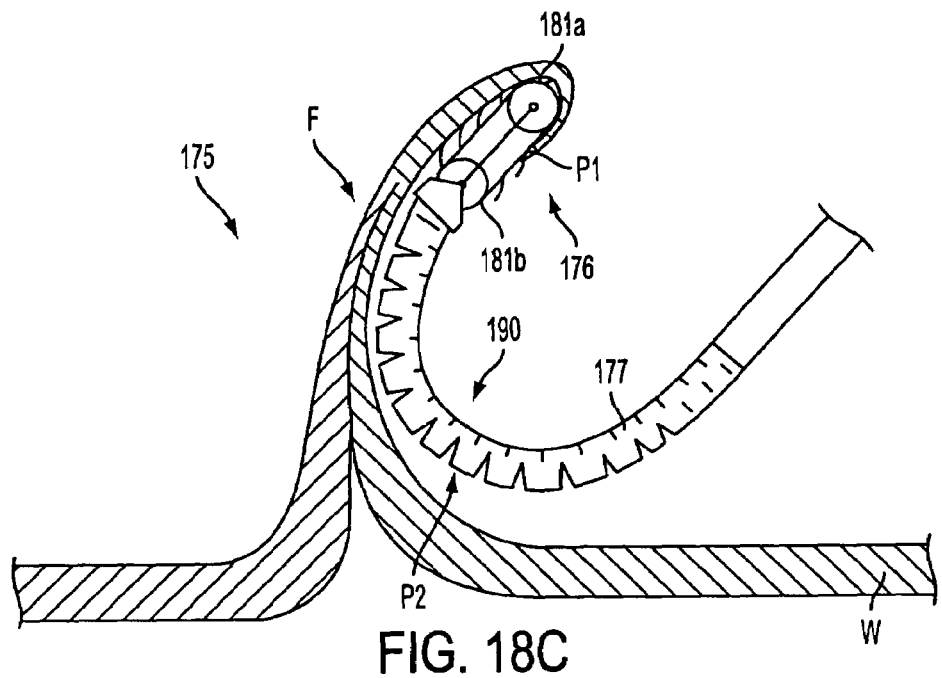

As depicted in FIG. 18C, once tissue wall W is securely engaged to treadmill assembly 176, distal end 174 of flexible tube 177 may be articulated in bendable section 190, thereby moving treadmill assembly 176 away from tissue wall W. The articulation of flexible tube 177 may be accomplished using a control wire and actuator disposed at the proximal end of the catheter, as previously described with respect to the embodiment of FIG. 1. By moving the treadmill assembly away from tissue wall W, additional tissue is pulled proximally and tissue fold F becomes elongated.

Figure 18D:
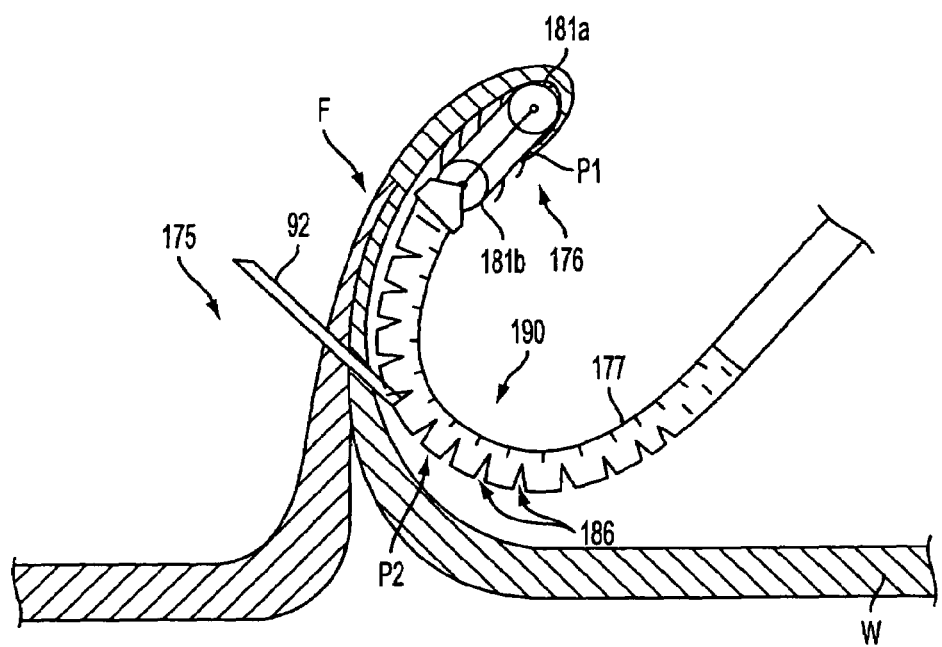

In FIG. 18D, tissue fold F is stretched across bendable section 190 of flexible tube 177 to create contact point P2. This permits a sharpened needle or obturator to be extended through one of slots 186 of bendable section 190 and across all four layers of the tissue wall W. Advantageously, stretching of tissue fold F across bendable section 190 permits an anchor to be ejected through both the muscularis and serosa layers, thus providing a durable foundation for gastrointestinal tissue approximation. For example, needle 192 may be extended through slot 186 in bendable section 190, and through the base of tissue fold F, and an anchor assembly (such as described with respect to any of FIGS. 4-17) may be ejected from needle 192 to secure the fold. Alternatively, an obturator (such as described with respect to FIGS. 5A and 5B) may be used to pierce the tissue fold at contact point P2 and deliver the anchor assembly. Treadmill assembly 176 may be disengaged from tissue wall W by reversing the rotation of proximal hub 181*b*.

Figure 20A:
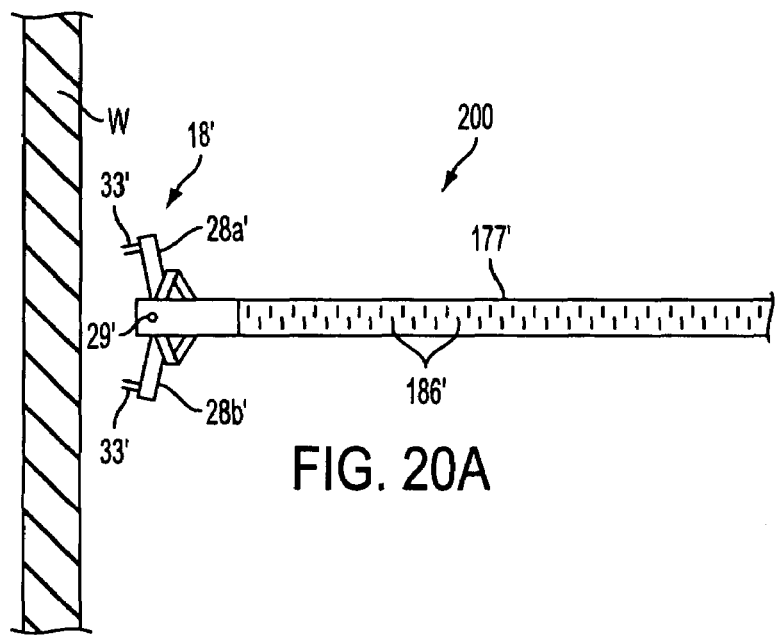
FIGS. 20A-20D are side views of further alternative apparatus for forming a gastrointestinal tissue fold in accordance with the principles of the present invention.

Referring now to FIG. 20A, a further alternative embodiment of apparatus for forming a tissue fold in accordance with the principles of the present invention is described. Apparatus 200 comprises tissue grabbing assembly 18' coupled to the distal end of a flexible tube 177', such as described with respect to the embodiment of FIG. 18. Flexible tube 177' preferably includes a plurality of through-wall slots 186' to enhance flexibility of the tube, yet maintain torqueability. In addition, flexible tube 177' may be made from stainless steel with an etched or laser-cut slot pattern, such as a sinusoidal repeating pattern of slots perpendicular to the longitudinal axis of the tube.

Tissue grabbing assembly 18' is similar to that described with respect to the embodiment of FIG. 1, and comprises a pair of jaws 28*a'*, 28*b'* arranged to rotate about pivot point 29' between an open configuration and a closed configuration. Each of jaws 28*a'*, 28*b'* preferably includes sharpened teeth 33' disposed near its distal end to facilitate grasping tissue wall W.

Figure 20B:
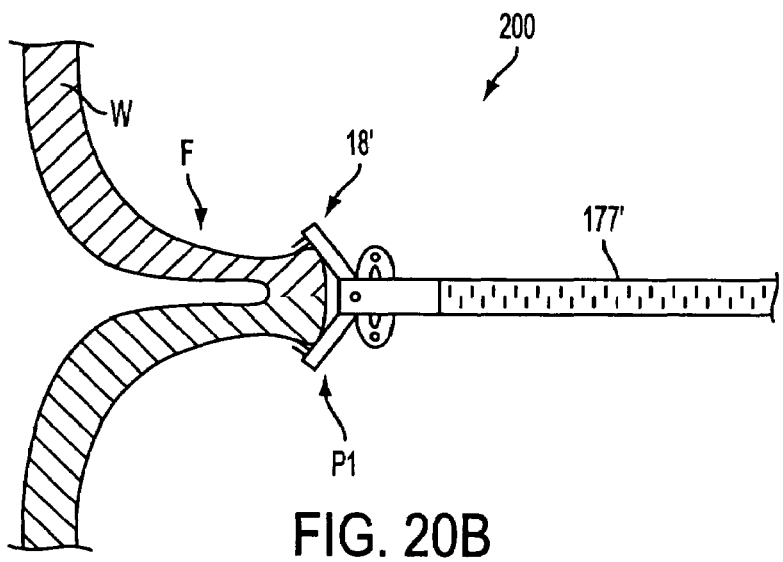

With respect to FIG. 20A, tissue grabbing assembly 18' is positioned transesophageally adjacent to tissue wall W and jaws 28*a'*, 28*b'* are moved to the open position. Tissue grabbing assembly 18' then is moved into contact with tissue wall W. As depicted in FIG. 20B, tissue grabbing assembly 18' is used to grab the tissue wall at a first contact point P1. After capturing a portion of tissue wall W within jaws 28*a'*, 28*b'*, flexible tube 177' is urged proximally to stretch tissue wall W and create tissue fold F.

Figure 20C:
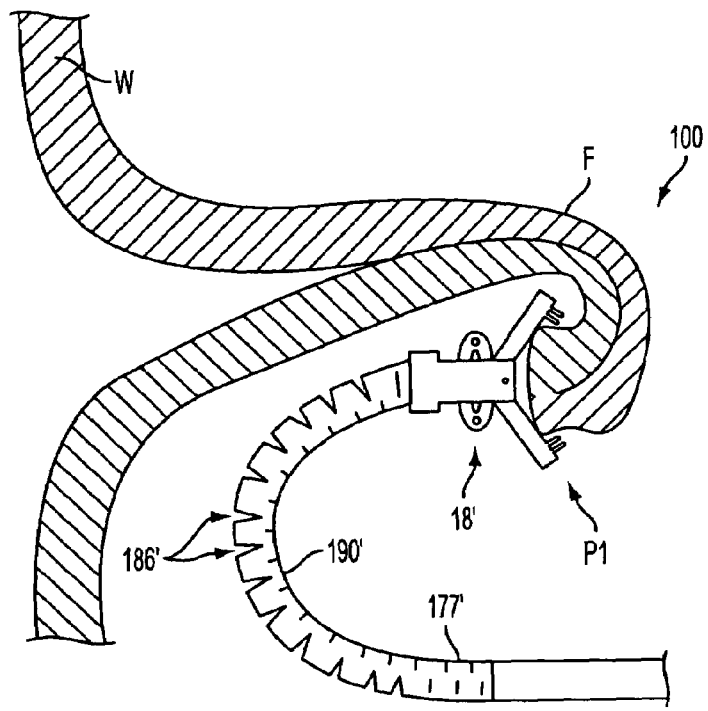

Referring to FIG. 20C, once tissue fold F is formed, the distal end of flexible tube 177' is articulated about bendable section 190' to move tissue grabbing assembly 18' away from tissue wall W. Articulation of flexible tube 177' may be controlled using an actuator disposed at the proximal end of the catheter, thus causing tissue fold F to become elongated.

Figure 20D:
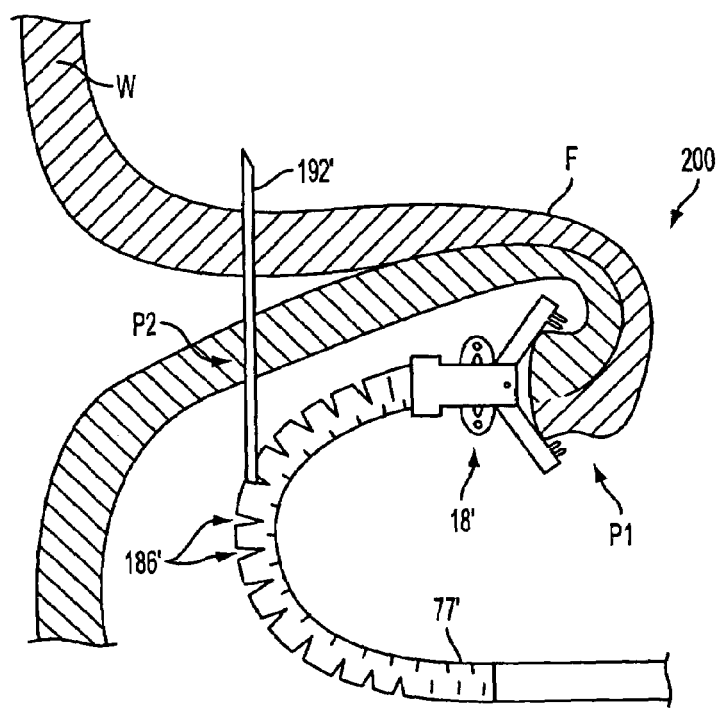

In FIG. 20D, tissue fold F is shown stretched across bendable section 190' so that a sharpened needle or obturator may be extended from one of slots 186' in bendable section 190' and across all four layers of the tissue wall W. Needle 192' then may be extended from slot 186' in bendable section 190' through contact point P2 and tissue fold F. An anchor assembly (e.g., as described with respect to any of FIGS. 4-17) then may be ejected from needle 192' to secure the fold. Alternatively, an obturator (e.g., as described with respect to FIGS. 5A and 5B) may be used to pierce the tissue fold at contact point P2 and deliver the anchor assembly.

With reference now to FIG. 21, an anchor delivery system adapted for use with the adjustable anchor assemblies of FIGS. 7-17 is described. In FIG. 21, the anchor delivery system is illustratively shown in use with anchor assembly 60 of FIG. 7, but this should in no way be construed as limiting. Also, the delivery system of FIG. 21 may be used in conjunction with apparatus for forming a tissue fold, such as apparatus 10, 175 and 200 described previously, in order to anchor the tissue fold; or may be used for any other application, or in conjunction with any other apparatus, requiring delivery of an anchor assembly.

Figure 21A:
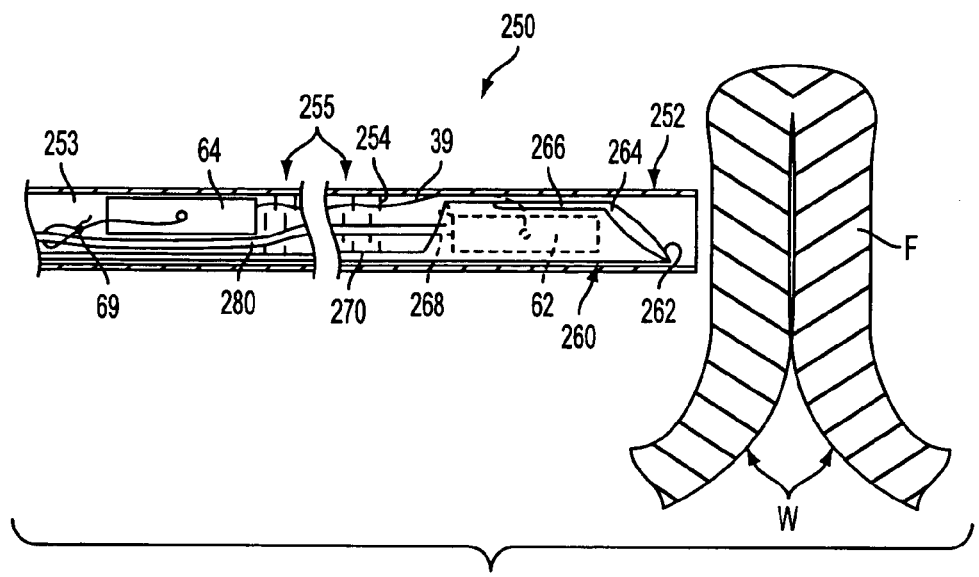
FIGS. 21A-21G are schematic side-sectional views of an anchor delivery system adapted for use with the adjustable anchor assemblies of FIGS. 7-17, illustrating a method of delivering the unidirectionally adjustable anchor assembly of FIG. 7 across a tissue fold.

In FIG. 21A, a distal region of anchor delivery system 250 is disposed adjacent tissue fold F in tissue wall W. Anchor delivery system 250 comprises flexible delivery tube 252 having lumen 253. Flexible delivery tube 252 may be configured for insertion through a patient's mouth and esophagus into a gastrointestinal lumen, such as the stomach. Lumen 253 of delivery tube 252 preferably has a diameter of less than about 3 cm, and even more preferably has a diameter of about 2.5 cm. Flexible delivery tube 252 preferably includes a plurality of through-wall slots 254 to enhance flexibility of the tube, yet maintain torqueability. Slots 254 may form bendable section 255. Preferably, flexible delivery tube 252 is made from stainless steel with an etched or laser-cut slot pattern. The slot pattern is preferably a sinusoidal repeating pattern of slots perpendicular to the longitudinal axis of the tube.

Anchor delivery system 250 further comprises delivery needle 260. Needle 260 preferably has a length of less than 2 cm, and even more preferably has a length of about 1.5 cm. Needle 260 preferably comprises sharpened distal tip 262, lumen 264, slot 266 extending proximally from distal tip 262, and proximal eyelet 268.

Lumen 264 of needle 260 is dimensioned such that a distal anchor may be disposed therein. As discussed previously, anchor delivery system 250 is illustratively described in conjunction with anchor assembly 60 of FIG. 7. In FIG. 21A, distal anchor 62 is disposed within lumen 264 of needle 260. Suture 39 passes through slot 266 of the needle as the suture extends from distal anchor 62 to proximal anchor 64. Needle 260 preferably is disposed within lumen 253 of flexible delivery tube 252 distal of bendable section 255, while proximal anchor 64 preferably is disposed within delivery tube 252 proximal of bendable section 255.

In this arrangement, distal anchor 62 may be deployed through needle 260 while the bendable section is actuated or bent, e.g., when anchor delivery system 250 is used in conjunction with previously described plication apparatus. Proximal anchor 64 subsequently may be advanced through bendable section 255 after the bendable section has once again been straightened. The distance, or length, of suture 39 extending between distal anchor 62, which is disposed distal of the bendable section, and proximal anchor 64, which is disposed proximal of the bendable section, is preferably greater than or equal to about 2 cm, and is even more preferably greater than or equal to about 4 cm.

Needle 260 is proximally coupled to needle pushrod 270, which facilitates translation of the needle beyond a distal end of flexible delivery tube 252. Needle pushrod 270 extends to a control actuator disposed at a proximal end of anchor delivery system 250 (not shown). Pushrod 270 optionally may be spring-loaded (not shown), for example, to facilitate puncture of tissue wall W and passage of needle 260 through tissue fold F.

Anchor delivery system 250 further comprises anchor pushrod 280, which is removably disposed through eyelet 268 of needle 260, and is configured to eject distal anchor 62 from lumen 264 of needle 260. As with needle pushrod 270, anchor pushrod 280 extends to a control actuator disposed at a proximal end of anchor delivery system 250 (not shown). The actuators controlling pushrods 270 and 280 are preferably at least partially coupled so that relative motion between the two pushrods can be limited and/or eliminated, as needed. Pushrod 280 passes through the proximal loop of suture formed by knot 69 on suture 39, such that the suture loop is threaded between needle pushrod 270 and anchor pushrod 280. This facilitates unidirectional adjustment of the length of suture disposed between distal anchor 62 and proximal anchor 64, as described hereinbelow.

Figure 21B:
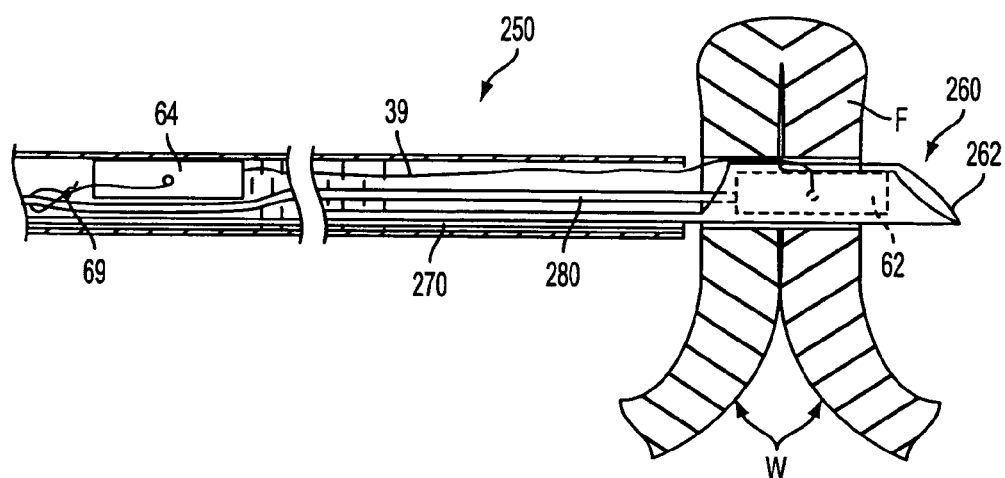
Figure 21C:
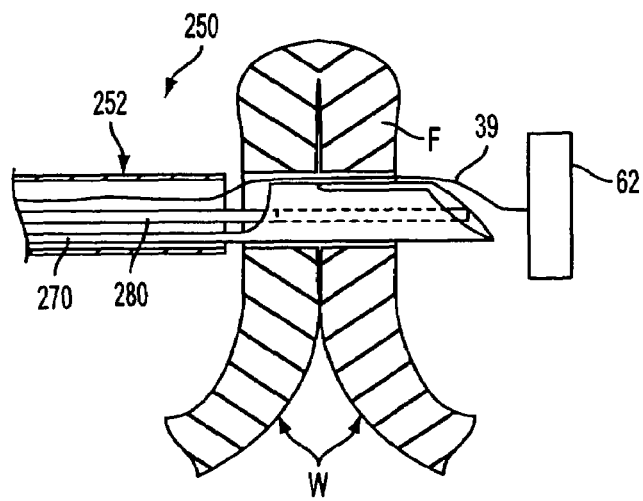

In FIG. 21B, pushrods 270 and 280 are simultaneously distally advanced with sufficient force, e.g., via spring-loading, such that sharpened distal tip 262 of needle 260 pierces tissue wall W and is advanced across fold F. Bendable section 255 of flexible delivery tube 252 optionally may be bent during advancement of the needle, as described previously with respect to the plication apparatus (see FIG. 3E). Anchor pushrod 280 is then advanced distally with respect to needle pushrod 270 and needle 260, such that it abuts distal anchor 62 and ejects the anchor from lumen 264 of needle 260 on the distal side of tissue fold F, as seen in FIG. 21C. Suture 39 likewise is ejected from slot 266 and disposed across fold F.

During delivery, the longitudinal axis of distal anchor 62 is substantially parallel to the longitudinal axis of needle 260. However, once anchor 62 has been ejected from needle 260, suture tension induces the anchor to rotate approximately 90° about its longitudinal axis, so that its longitudinal axis is substantially perpendicular to the longitudinal axis of needle 260. This rotation of distal anchor 62 prevents it from being pulled back through tissue wall W. One or both ends of anchor 62 may be flared outward (not shown) to facilitate such rotation upon contact with the tissue wall.

Figure 21D:
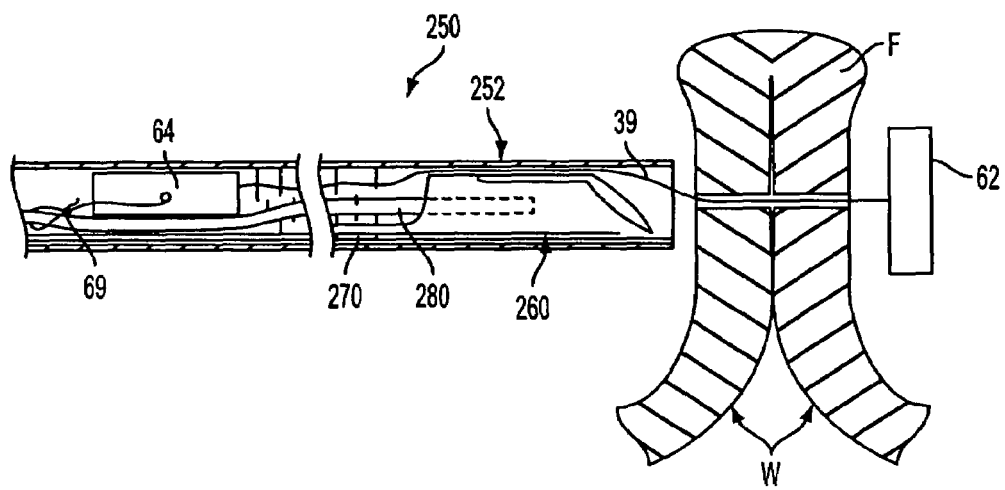

In FIG. 21D, anchor pushrod 280 is retracted proximally within lumen 264 of needle 260, the needle is retracted within flexibly delivery tube 252 via pushrod 270, and then delivery system 250 is retracted proximally across tissue fold F. Distal anchor 62 is disposed on the distal side of the tissue fold, suture 39 extends through the fold, and proximal anchor 64 is disposed on the proximal side of the fold within delivery tube 252. If bendable section 255 were flexed during deployment of distal anchor 62 (see FIG. 3E), it is straightened to facilitate delivery of the proximal anchor.

Figure 21E:
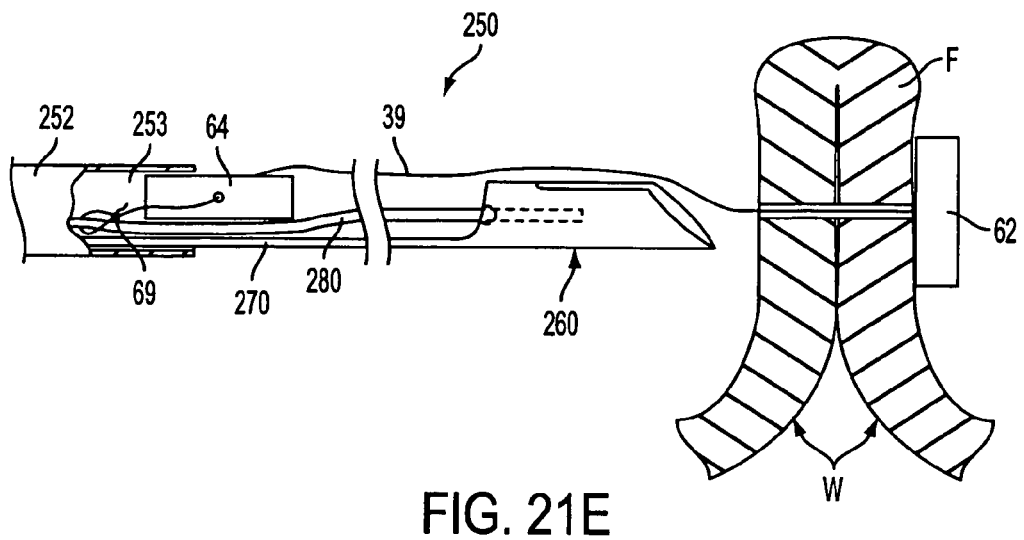

Delivery tube 252 is then retracted proximally with respect to pushrods 270 and 280, causing needle 260 to exit lumen 253 of the delivery tube on the proximal side of tissue fold F, thereby providing space for proximal anchor 64 to exit the lumen. Next, delivery tube 252 or the full delivery system 250 is retracted, such that proximal anchor 64 is ejected from delivery tube lumen 253, as seen in FIG. 21E. Delivery tube 252 is then re-advanced and/or pushrods 270 and 280 are simultaneously retracted, such that needle 260 is repositioned within lumen 253 of the delivery tube.

Figure 21F:
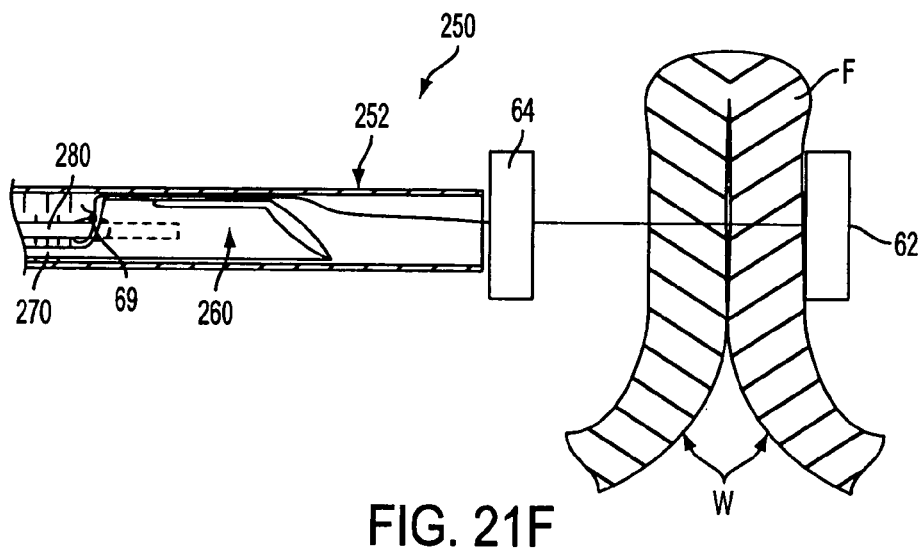

Flexible delivery tube 252 is advanced with respect to needle 260, such that it pushes proximal anchor 64 distally. The proximal suture loop formed by knot 69 on suture 39 catches against the proximal end of needle 260 and anchor pushrod 280, which pulls distal anchor 62 taut against tissue fold F, as seen in FIG. 21F. Continued advancement of delivery tube 252 unidirectionally adjusts, i.e. shortens, length L of suture 39 disposed between distal anchor 62 and proximal anchor 64, while forcing proximal anchor 64 against the tissue fold and firmly anchoring the fold between the proximal and distal anchors.

Figure 21G:
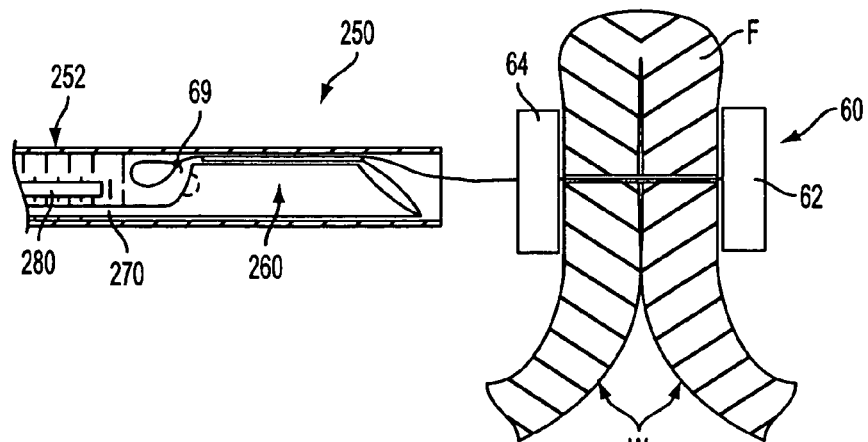

Once length L has been adjusted such that anchor assembly 60 firmly anchors tissue fold F in position, anchor pushrod 280 may be retracted proximally with respect to needle pushrod 270 and needle 260, such that the distal end of anchor pushrod 280 is proximally retracted through eyelet 268 and out of needle 260. As seen in FIG. 21G, the suture loop formed by knot 69 on suture 39 slips off the distal end of anchor pushrod 280, removing anchor assembly 60 from anchor delivery system 250 and allowing the anchor delivery system to be removed from the patient.

Delivery system 250 optionally may comprise cutting apparatus (not shown) for removing the portion of suture extending proximally of proximal anchor 64 post-adjustment. Alternatively, secondary apparatus may be provided to remove such proximal length of suture. As yet another alternative, the unneeded length of suture may be left within the patient post-procedure.

In order to decrease the number of steps required to deliver and adjust anchor assembly 60, once distal anchor 62 has been deployed, as in FIG. 21C, the entire anchor delivery system 250 may be retracted proximally, such that needle 260 is retracted across tissue fold F while still disposed outside of delivery tube lumen 253. This is in contrast to the method described with respect to FIG. 21D, wherein the needle is disposed within the delivery tube prior to retraction across the tissue fold. Continued proximal retraction of anchor delivery system 250 or delivery tube 252 deploys proximal anchor 64 from delivery tube lumen 253. Anchor assembly 60 then may be unidirectionally adjusted, as described previously.

As will be apparent to those of skill in the art, when anchor delivery system 250 is used in conjunction with previously described apparatus 10, 175 or 200, to place an anchor assembly across fold F formed by said apparatus, flexible delivery tube 252 may either comprise or be advanced through flexible tube 14, 177 or 177', of apparatus 10, 175 or 200, respectively. Likewise needle 260 may comprise needle 34, 92 or 92', of apparatus 10, 175 or 200, respectively. Needle 260 may alternatively comprise obturator 50 of FIG. 5.

Referring now to FIG. 22, an alternative anchor delivery system is described. As with anchor delivery system 250 of FIG. 21, anchor delivery system 300 of FIG. 22 is adapted for use with the adjustable anchor assemblies of FIGS. 7-17. In FIG. 22, the anchor delivery system 300 is illustratively shown in use with anchor assembly 60 of FIG. 7, but this should in no way be construed as limiting. Also, delivery system 300 may be used in conjunction with apparatus for forming a tissue fold, such as apparatus 10, 175 and 200 described previously, in order to anchor the tissue fold; or may be used for any other application, or in conjunction with any other apparatus, requiring delivery of an anchor assembly.

Figure 22A:
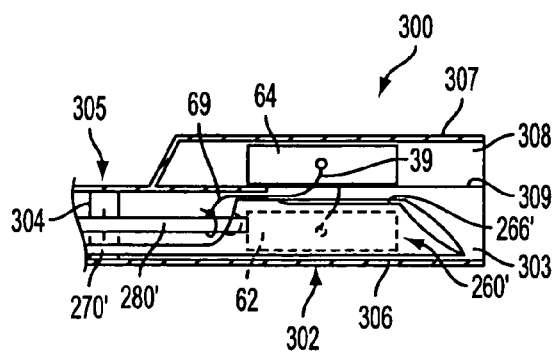
FIGS. 22A and 22B are, respectively, a schematic sideview, partially in section, and an end-view of an alternative anchor delivery system adapted for use with the adjustable anchor assemblies of FIGS. 7-17, wherein the proximal anchor is disposed within a separate delivery tube.

FIG. 22A illustrates a distal region of anchor delivery system 300. System 300 comprises flexible delivery tube 302 having lumen 303. Flexible delivery tube 302 may be configured for insertion through a patient's mouth and esophagus into a gastrointestinal lumen, such as the stomach. Flexible delivery tube 302 preferably includes a plurality of through-wall slots 304 to enhance flexibility of the tube, yet maintain torqueability. Slots 304 may form bendable section 305. Preferably, flexible delivery tube 302 is made from stainless steel with an etched or laser-cut slot pattern. The slot pattern is preferably a sinusoidal repeating pattern of slots perpendicular to the longitudinal axis of the tube.

Figure 22B:
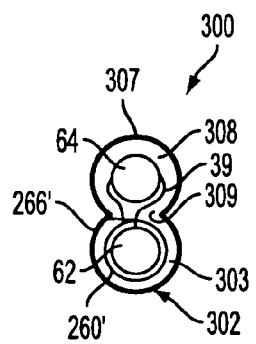

Flexible delivery tube 302 further comprises end region 306, which is coupled to anchor tube 307 having lumen or bore 308. As best seen in FIG. 22B, lumen 308 of anchor tube 307 communicates with lumen 303 of delivery tube 302 via through-slot 309. Proximal anchor 64 is disposed within anchor tube 307, while distal anchor 62 is disposed within needle 260', which sits within delivery tube 302.

Suture 39 passes out of needle 260' from distal anchor 62 through slot 266'. It then crosses from flexible delivery tube 302 to anchor tube 307 via through-slot 309. After passing through proximal anchor 64, suture 39 is passed back to delivery tube 302 via the through-slot, and is threaded around anchor pushrod 280', such that the loop of suture formed by knot 69 on suture 39 is disposed between needle pushrod 270' and anchor pushrod 280'.

Needle 260', needle pushrod 270' and anchor pushrod 280' are substantially the same as needle 260 and pushrods 270 and 280, respectively, which are described hereinabove with respect to anchor delivery system 250 of FIG. 21. Furthermore, anchor assembly 60 may be delivered from and adjusted by anchor delivery system 300 in a manner similar to that described hereinabove with respect to system 250.

In FIG. 22A, anchor tube 307 of anchor delivery system 300 is illustratively shown as a relatively short tube having lumen or bore 308 adapted for disposal of proximal anchor 64 therein. However, it should be understood that anchor tube 307, lumen 308 and/or through-slot 309 alternatively may extend all or part of the way to a proximal end of flexible delivery tube 302 of delivery system 300. Advantageously, such an arrangement facilitates loading of anchor assembly 60 from a proximal end of the anchor delivery system and may simplify manufacturing of the system.

Anchor delivery system 300 illustratively has been described with a single anchor assembly 60 disposed therein. However, it should be understood that a plurality of anchor assemblies may be loaded within delivery system 300, thereby facilitating delivery of multiple anchor assemblies across different points of a tissue fold, across different (e.g., adjacent) tissue folds, or across other tissue structures. The plurality of distal anchors 62 preferably are loaded within needle 262' of flexible delivery tube 302, while the plurality of proximal anchors 64 preferably are loaded within lumen 308 of anchor tube 307.

An advantage of anchor delivery system 300, as compared to system 250 of FIG. 21, is that both the proximal and distal anchors are located distal of the bendable section of the delivery tube during delivery. This reduces an initial length of suture that must be disposed between the anchors, thereby reducing a length of unneeded suture extending proximally of the proximal anchor post-delivery and adjustment. It also simplifies delivery by allowing both the proximal and distal anchors to be delivered while the bendable section of the delivery tube is bent. Additionally, placement of the proximal anchor in a separate anchor tube eliminates a need to eject the needle from the flexible delivery tube on the proximal side of a tissue fold in order to deploy the proximal anchor, thereby reducing a risk of accidental tissue puncture with the needle.

Figure 23:
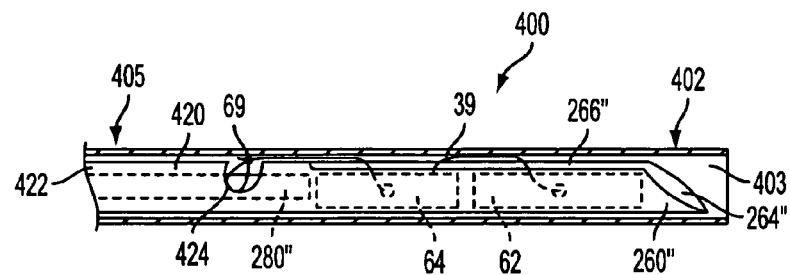
FIG. 23 is a schematic side-sectional view of an alternative anchor delivery system adapted for use with the adjustable anchor assemblies of FIGS. 7-17, wherein both the proximal and distal anchors are loaded within the needle.

With reference to FIG. 23, another alternative anchor delivery system is described. As with anchor delivery systems 250 and 300 of FIGS. 21 and 22, respectively, anchor delivery system 400 of FIG. 23 is adapted for use with the adjustable anchor assemblies of FIGS. 7-17. Anchor delivery system 400 is illustratively shown in use with anchor assembly 60 of FIG. 7, but this should in no way be construed as limiting. Also, delivery system 400 may be used in conjunction with apparatus for forming a tissue fold, such as apparatus 10, 175 and 200 described previously, in order to anchor the tissue fold; or may be used for any other application, or in conjunction with any other apparatus, requiring delivery of an anchor assembly.

FIG. 23 illustrates a distal region of anchor delivery system 400. System 400 comprises flexible delivery tube 402 having lumen 403. Flexible delivery tube 402 may be configured for insertion through a patient's mouth and esophagus into a gastrointestinal lumen, such as the stomach. Flexible delivery tube 402 preferably includes a plurality of through-wall slots to enhance flexibility of the tube, yet maintain torqueability. The slots may form bendable section 405.

Anchor delivery system 400 further comprises delivery needle 260", which is disposed within lumen 403 of flexible delivery tube 402 distal of bendable section 405 during delivery. As discussed previously, anchor delivery system 400 is illustratively described in conjunction with anchor assembly 60 of FIG. 7. Needle 260" preferably has a length sufficient for both distal anchor 62 and proximal anchor 64 of anchor assembly 60 to be disposed therein; for example, needle 260" preferably has a length of less than about 5 cm, and even more preferably has a length of about 3 cm. Except for an increase in length, needle 260" is substantially the same as needle 260 of FIG. 21.

In FIG. 23, both distal anchor 62 and proximal anchor 64 are disposed within lumen 264" of needle 260". Suture 39 passes through and back through slot 266" of the needle as the suture extends from distal anchor 62 to proximal anchor 64. Alternatively the length of suture between the proximal and distal anchors may be disposed within the needle during delivery. Advantageously, both the proximal and distal anchors of anchor assembly 60 may be deployed through needle 260" while bendable section 405 is actuated or bent, e.g., while anchor delivery system 400 is used in conjunction with previously described plication apparatus.

Needle 260" is proximally coupled to flexible needle pushtube 420, which facilitates translation of the needle beyond a distal end of flexible delivery tube 402. As will be apparent to those of skill in the art, needle 260" and needle pushtube 420 optionally may be manufactured as a single piece. Needle pushtube 420 comprises lumen 422, as well as skive 424 that communicates with lumen 422. Needle pushtube 420 extends to a control actuator (not shown), which may be spring-loaded, disposed at a proximal end of anchor delivery system 400.

Anchor pushrod 280", which is substantially the same as anchor pushrod 280 described previously, is removably disposed within lumen 422 of needle pushtube 420 distal of skive 424. As with pushtube 420, anchor pushrod 280" extends to a control actuator (not shown) disposed at a proximal end of the anchor delivery system. Suture 39 proximally extends from proximal anchor 64 through slot 266" of needle 260", through skive 424 and within lumen 422 of needle pushtube 420, around anchor pushrod 280" and out through skive 424 to knot 69. The proximal loop of suture formed by knot 69 is trapped around pushrod 280" and within lumen 422 of the needle pushtube, thereby facilitating unidirectional adjustment of the length of suture disposed between distal anchor 62 and proximal anchor 64. As an alternative to the proximal loop of suture, knot 69 may be formed on the proximal end of suture 39, such that the knot is trapped between anchor pushtube 280" and needle pushrod 420 (see knot K of FIG. 24).

Anchor assembly 60 may be delivered from and adjusted by anchor delivery system 400 in a manner similar to that described hereinabove with respect to system 250 of FIG. 21, with a few alterations. Specifically, during deployment of distal anchor 62, anchor pushrod 280" is advanced against proximal anchor 64, which in turn advances in-line distal anchor 62. The pushrod is advanced a sufficient distance with respect to needle 260" to eject the distal anchor from needle lumen 264", but not so far as to also prematurely eject proximal anchor 64. Motion limitation apparatus may be provided to ensure that the distal anchor is not prematurely ejected. Exemplary motion limitation apparatus is described hereinbelow with respect to FIG. 24; additional apparatus, per se known, will be apparent.

In order to eject proximal anchor 64 from lumen 264" of needle 260", either the needle is retracted until length L of suture 39 disposed between the proximal and distal anchors is pulled taut and pulls the proximal anchor out of the needle lumen, or anchor pushrod 280" is advanced a sufficient distance within the lumen of needle 260" to eject the proximal anchor from the lumen (or a combination thereof). Additionally, in order to release anchor assembly 60 from anchor delivery system 400 post-delivery and adjustment, anchor pushrod 280" is retracted proximal of skive 424 such that the loop of suture 39 formed by knot 69 is no longer trapped within lumen 422 of needle pushrod 420.

A significant advantage of anchor delivery system 400, as compared to system 250 of FIG. 21, is that both the proximal and distal anchors are disposed distal of bendable section 405 of flexible delivery tube 402. A significant advantage of anchor delivery system 400, as compared to system 300 of FIG. 22, is that both the proximal and distal anchors are disposed within needle 260", thereby eliminating a need for an anchor tube and reducing the profile of the system.

Figure 24:
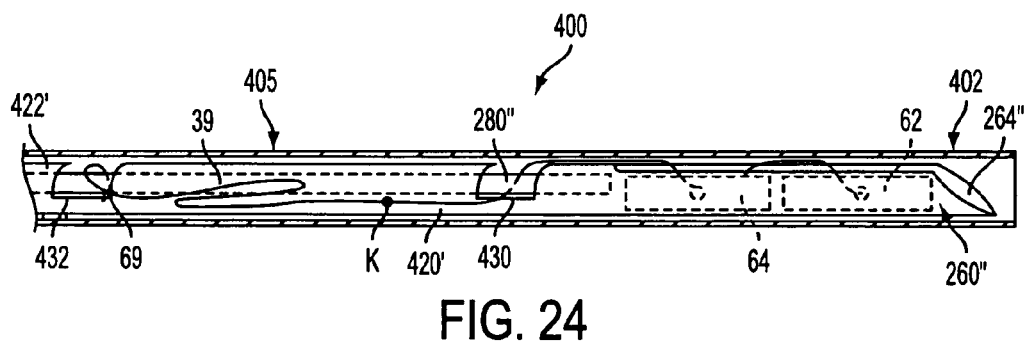
FIG. 24 is a schematic side-sectional view of an alternative embodiment of the anchor delivery system of FIG. 23 comprising motion limitation apparatus.

Referring now to FIG. 24, an alternative embodiment of anchor delivery system 400 is described comprising motion limitation apparatus. Anchor delivery system 400' is substantially the same as system 400, except that needle pushrod 420' comprises two skives: motion limitation skive 430 and unidirectional adjustment skive 432, both of which communicate with lumen 422' of the needle pushrod. Suture 39 proximally extends from proximal anchor 64, through motion limitation skive 430 and within lumen 422' between anchor pushrod 280" and needle pushtube 420'. Suture 39 exits skive 430 and is tied off at motion limitation knot K, which is trapped at skive 430 by anchor pushrod 280". Suture 39 then continues proximally to unidirectional adjustment skive 432 and the proximal loop of suture formed by knot 69, which is trapped at skive 432 around pushrod 280".

A length of suture extending between proximal anchor 64 and knot K is specified such that distal anchor 62 may exit lumen 264" of needle 260", but proximal anchor 64 cannot while knot K is trapped at skive 430 by anchor pushrod 280". For example, during delivery of anchor assembly 60 across a tissue fold, advancement of pushrod 280" advances proximal anchor 64, which in turn advances in-line distal anchor 62 until the distal anchor is ejected from needle lumen 264" on the distal side of the tissue fold. Knot K limits a distance anchor pushrod 280" may be advanced and ensures that proximal anchor 64 is not prematurely deployed.

Once anchor delivery system 400' is again disposed on the proximal side of the tissue fold, anchor pushrod 280" is retracted proximal of motion limitation skive 430, thereby allowing knot K to escape from skive 430 and facilitating deployment of proximal anchor 64. Proximal anchor 64 may be deployed by either retracting needle 260" until the length of suture between the two anchors is pulled taut and pulls the proximal anchor out of the needle, or by re-advancing pushrod 280" to push the proximal anchor out of the needle.

The anchor assembly may then be unidirectionally adjusted via the suture loop trapped at skive 232, as described previously. After adjustment has been completed, anchor pushrod 280" is retracted proximal of unidirectional adjustment skive 432, thereby allowing the loop of suture formed by knot 69 of suture 39 to escape from skive 432. A significant advantage of anchor delivery system 400', as compared to system 400 of FIG. 23, is that motion limitation skive 430 reduces a risk of premature deployment of proximal anchor 64.

Although preferred illustrative embodiments of the present invention are described hereinabove, it will be apparent to those skilled in the art that various changes and modifications may be made thereto without departing from the invention. It is intended in the appended claims to cover all such changes and modifications that fall within the true spirit and scope of the invention.

What is claimed is:

1. Apparatus for securing a tissue fold within a patient, the apparatus comprising:
an elongate member having a proximal end and a distal end;
application apparatus extending from the distal end of said elongate member and having a distal portion adapted to engage a tissue fold within a patient; and
an anchor assembly having proximal and distal anchors connected by a suture, said suture having a proximal end and a distal end,
wherein the anchor assembly is adapted for adjustment of the length of suture disposed between the proximal and distal anchors while the anchor assembly is disposed across the tissue fold;
further comprising an anchor delivery system adapted to deploy and secure the anchor assembly across the tissue fold;
wherein the anchor delivery system comprises a flexible delivery tube having a lumen, and a hollow needle disposed within the lumen, said anchor delivery system having a distal region extending from the distal end of said elongate member;
wherein the distal anchor passes through the hollow needle during delivery;
wherein the anchor delivery system further comprises an anchor tube coupled to a distal region of the flexible delivery tube, and wherein the proximal anchor is disposed within the anchor tube during delivery;
wherein the anchor delivery system further comprises a trap mechanism located substantially within the distal region of said anchor delivery system, said trap mechanism being adapted to reversibly trap the suture at or near its proximal end to facilitate adjustment of the length of suture disposed between the proximal and distal anchors, and wherein the trap mechanism is adapted to release the suture after the length of suture has been adjusted.

2. Apparatus for securing a tissue fold within a patient, the apparatus comprising:
an elongate member having a proximal end and a distal end;
application apparatus extending from the distal end of said elongate member and having a distal region adapted to engage a tissue fold within a patient; and
an anchor assembly having proximal and distal anchors connected by a suture, said suture having a proximal end and a distal end,
wherein the anchor assembly is adapted for adjustment of the length of suture disposed between the proximal and distal anchors while the anchor assembly is disposed across the tissue fold;
further comprising an anchor delivery system adapted to deploy and secure the anchor assembly across the tissue fold;
wherein the anchor delivery system comprises a flexible delivery tube having a lumen, and a hollow needle disposed within the lumen, said anchor delivery system having a distal region extending from the distal end of said elongate member;
wherein the anchor assembly passes through the hollow needle during delivery;
wherein the anchor delivery system further comprises a trap mechanism located substantially within the distal region of said anchor delivery system, said trap mechanism being adapted to reversibly trap the suture at or near its proximal end to facilitate adjustment of the length of suture disposed between the proximal and distal anchors, and wherein the trap mechanism is adapted to release the suture after the length of suture has been adjusted.

3. The apparatus of claim 2, further comprising an anchor pushrod in communication with an interior of the needle, the anchor pushrod adapted to eject the anchor assembly from the needle.

* * * * *